(12) United States Patent
Suzuki

(10) Patent No.: US 7,833,202 B2
(45) Date of Patent: Nov. 16, 2010

(54) METHOD OF GASTROSTOMY, AND AN INFECTION PREVENTIVE COVER, OR CATHETER KIT, AND A GASTROSTOMY CATHETER

(76) Inventor: Yutaka Suzuki, 1-2, Hakusan 2-chome, Guran Aruba Hakusan 601, Bunkyo-ku, Tokyo 112-0001 (JP)

( * ) Notice: Subject to any disclaimer, the term of this patent is extended or adjusted under 35 U.S.C. 154(b) by 1604 days.

(21) Appl. No.: 10/222,910

(22) Filed: Aug. 19, 2002

(65) Prior Publication Data
US 2003/0229334 A1     Dec. 11, 2003

(30) Foreign Application Priority Data
Jun. 10, 2002   (JP)   ............................. 2002-168854

(51) Int. Cl.
*A61M 5/00* (2006.01)
(52) U.S. Cl. ...................... 604/171; 604/910
(58) Field of Classification Search ............... 604/910, 604/535, 332, 93.01, 158–180, 31, 171, 174; 606/139
See application file for complete search history.

(56) References Cited

U.S. PATENT DOCUMENTS

| | | | | |
|---|---|---|---|---|
| 4,798,592 A | * | 1/1989 | Parks | 604/500 |
| 4,861,334 A | * | 8/1989 | Nawaz | 604/539 |
| 5,125,897 A | * | 6/1992 | Quinn et al. | 604/99.03 |
| 5,174,276 A | * | 12/1992 | Crockard | 600/104 |
| 5,582,165 A | * | 12/1996 | Bryan et al. | 128/207.14 |
| 6,322,538 B1 | * | 11/2001 | Elbert et al. | 604/174 |
| 6,535,764 B2 | * | 3/2003 | Imran et al. | 607/40 |
| 6,754,536 B2 | * | 6/2004 | Swoyer et al. | 607/40 |

FOREIGN PATENT DOCUMENTS

| | | |
|---|---|---|
| EP | 0 744 185 | 11/1996 |
| JP | 2001-224694 | 8/2001 |
| JP | 2001224694 A * | 8/2001 |

OTHER PUBLICATIONS

Japanese Office Action dated Oct. 14, 2008, with English translation.

* cited by examiner

*Primary Examiner*—Nicholas D Lucchesi
*Assistant Examiner*—Laura A Bouchelle
(74) *Attorney, Agent, or Firm*—McGinn IP Law Group PLLC

(57) ABSTRACT

Disclosed is an infection preventive catheter kit for preventing the infection of the wound. A percutaneous endoscopic gastrostomy (PEG) catheter 20 is inserted into an infection preventive cover 10, which is provided with a socket 13 at a distal end thereof. A head portion 15*a* of a guide wire 15 which is inserted into the PEG catheter 20 through a top end thereof and an in-stomach remaining member 23 provided at a distal end of the PEG catheter 20 are engaged with (fixed to) the socket 13 of the infection preventive cover 10 by a pin 14 penetrating the socket 13.

22 Claims, 20 Drawing Sheets

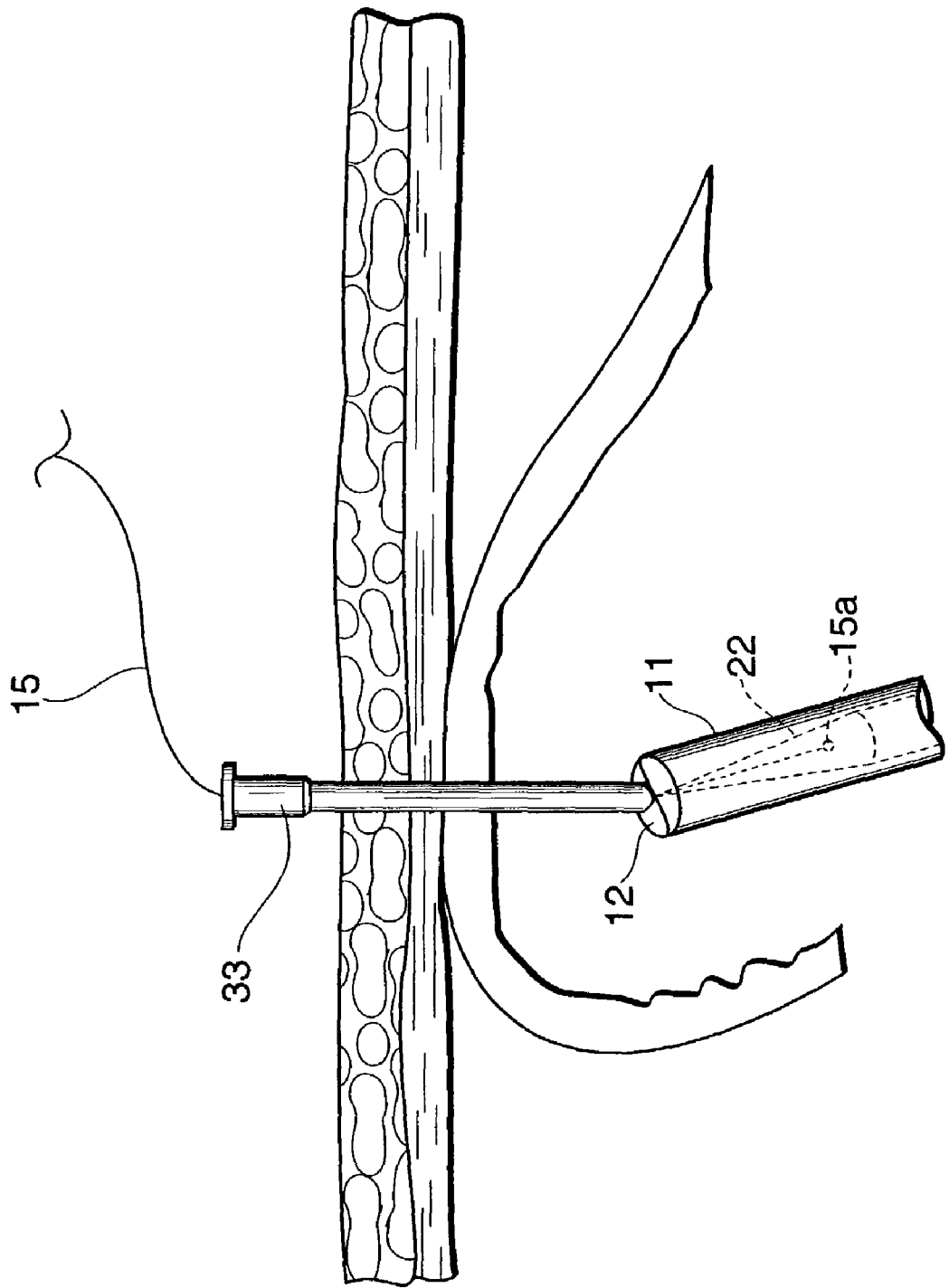

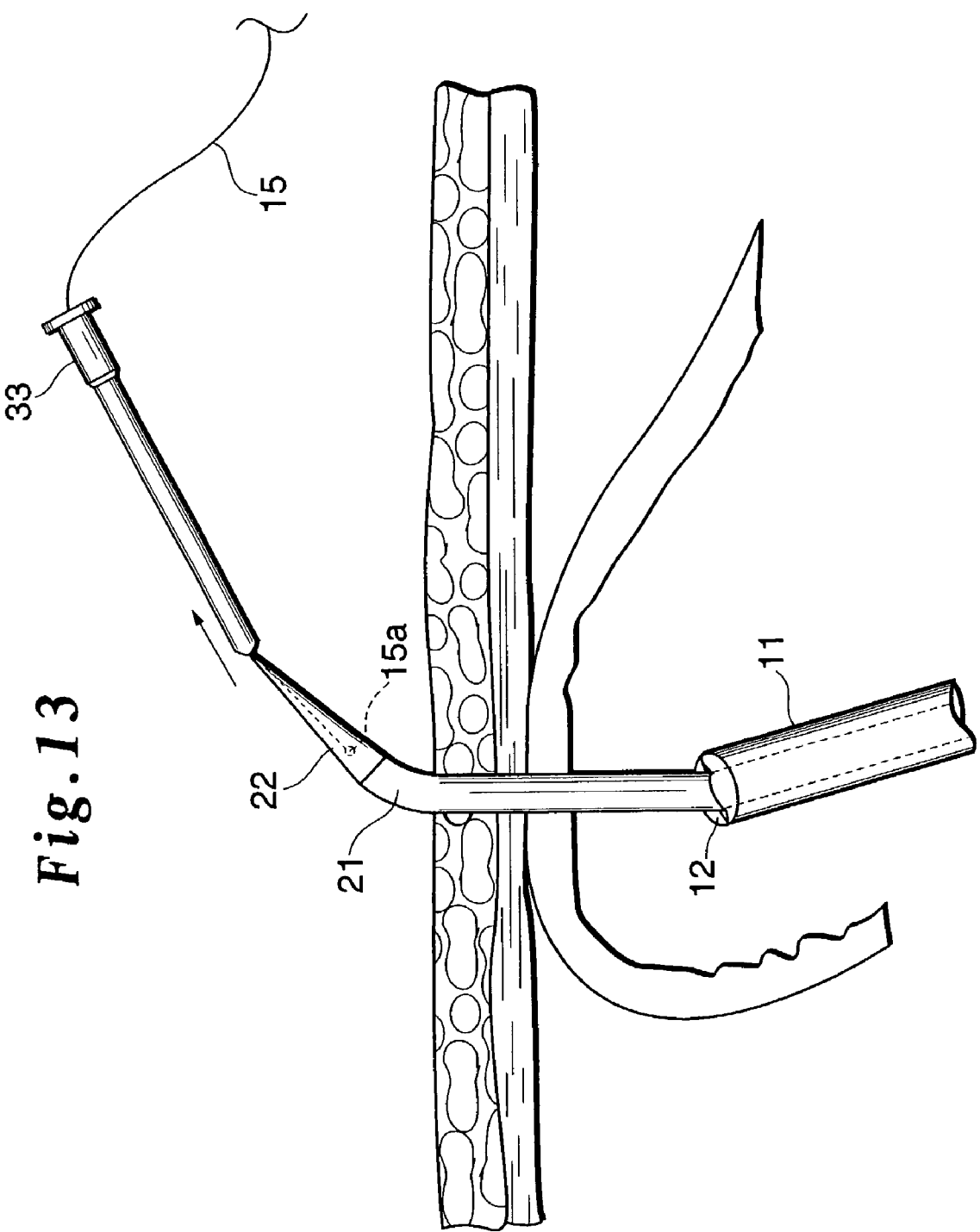

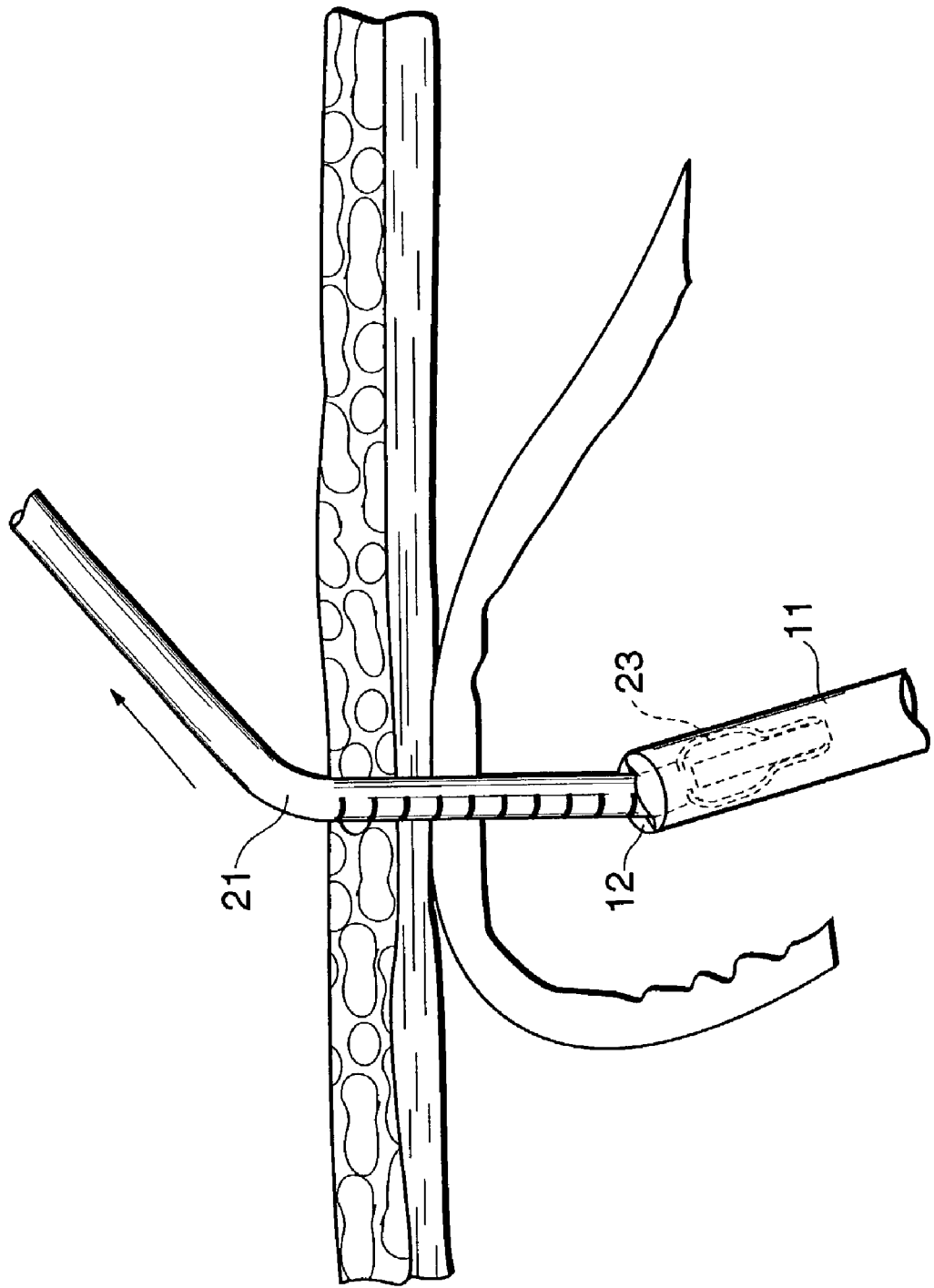

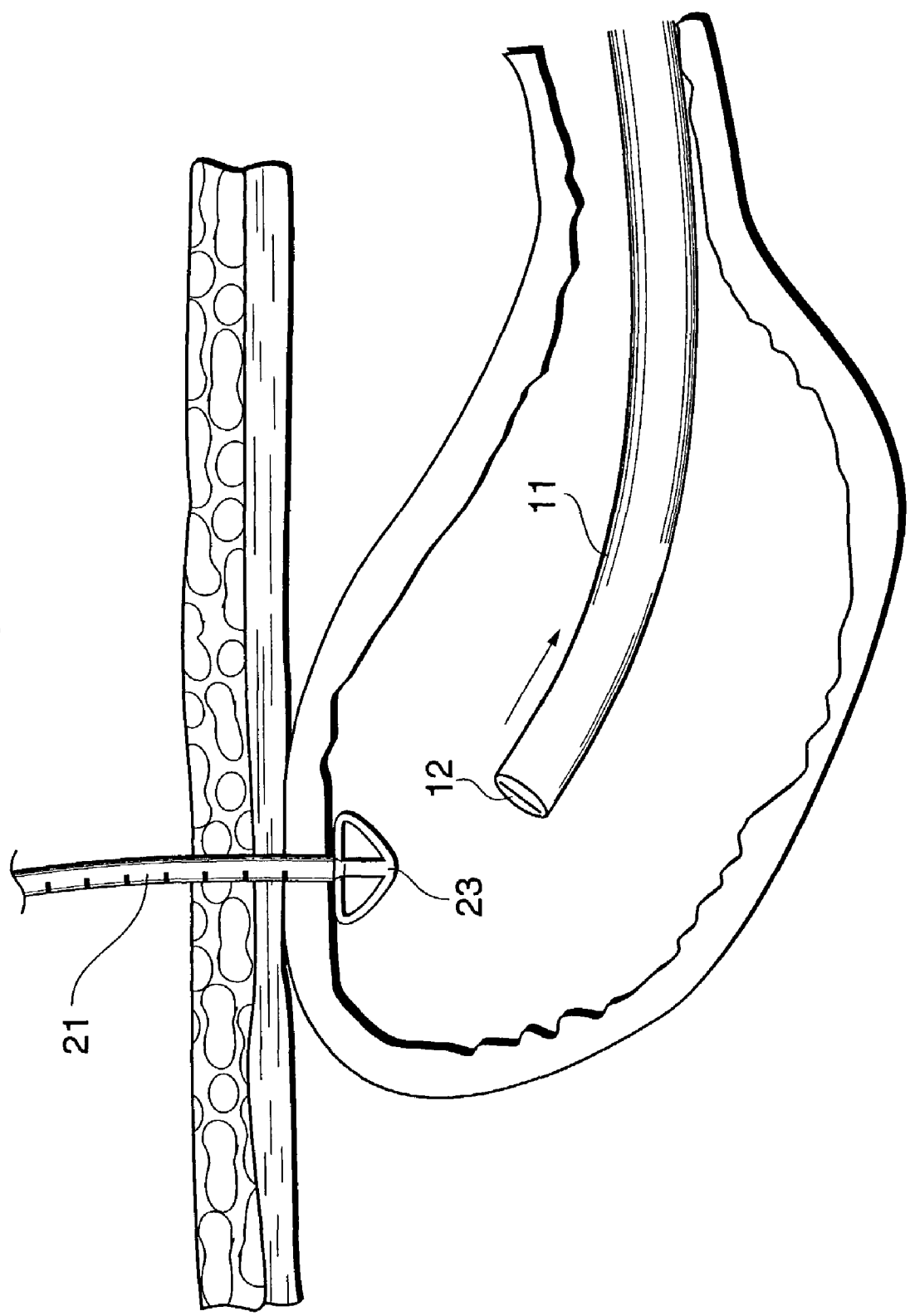

METHOD OF GASTROSTOMY, AND AN INFECTION PREVENTIVE COVER, OR CATHETER KIT, AND A GASTROSTOMY CATHETER

BACKGROUND OF THE INVENTION

1. Field of the Invention

The present invention relates to a method of gastrostomy and an infection preventive cover, or catheter kit and a gastrostomy catheter kit for use with the method.

2. Description of the Background Art

For a percutaneous endoscopic gastrostomy (PEG) enabling enteral feeding to a patient who finds difficulty in swallowing feeds or who cannot swallow, it is sufficient to apply a local anesthesia to the patient and the operation time is favorably short, i.e., about five to about ten minutes, and the patient can be quickly recovered after the operation. In a case where the patient in a good general condition after the operation, she or he may leave the hospital on the same day on which the operation is conducted. The PEG is therefore explosively developed worldwide. In the United States, for example, about 180,000 cases were reported in 1997. In the future, the number of the operations is expectedly increased in the world.

As commonly known, the PEG includes three methods, namely, "pull", "push", and "introduce" methods (techniques). Among these methods, the "pull" and "push" methods have been broadly adopted due to simplicity and safeness of the operation. However, these methods are attended with two drawbacks as follows.

The endoscope is required to be twice inserted in the pertinent patient, which leads to a problem of complex operations and pains to patients. There exists a fear of damage to the larynx, the upper pharynx or the esophagus.

The PEG catheter (including a PEG tube and an in-stomach remaining member (dome, etc.) connected to the tube) is infected in the oral cavity, the upper pharynx or the larynx and hence the wounded part of the patient is liable to be infected.

The first drawback above can be sufficiently removed by improving the sedation or anesthesia and by increasing the quality of skill of the endoscopist. However, the second drawback, i.e., the infection of the wound due to the contamination of the PEG tube and the in-stomach remaining member takes place with a high possibility. The literature of Europe and America reported about 35% to about 45% of the infection of wound. When the infection of wound occurs, antibiotics are required to be administered to the patient for a long period of time. This resultantly delays the starting point of the enteral feeding for the patient, and immunity of the patient from diseases is weakened, this may elongate the hospital treatment in some cases. The patient suffers from serious pains and the fee for medical treatment soars. Consequently, not only the patient but also family members of the patient must bear the expense and suffer from mental stress. When the cleaning of the oral cavity, the preoperation disinfection of the upper pharynx, and the preventive administration of antibiotics are completely carried out, the number of bacteria appearing on the PEG tube and the in-stomach remaining member can be decreased. However, this is not the basic countermeasure.

A trial for decreasing the number of bacteria appearing on the PEG tube and the in-stomach remaining member is conducted, in which the PEG tube and the in-stomach remaining member are fed into the stomach through the oral cavity, larynx, upper pharynx all esophagus in a state where they are enclosed with a cover. However it is just a trial but does not reach a level of practical use.

SUMMARY OF THE INVENTION

It is therefore an object of the present invention to provide a method of gastrostomy capable of preventing the infection of the wound.

Another object of the present invention is to provide an infection preventive cover to prevent the infection of the wound in the method of gastrostomy.

Still another object of the present invention is to provide an infection preventive catheter kit to prevent the infection of the wound in the method of gastrostomy.

Yet another object of the present invention is to provide a gastrostomy catheter to prevent the infection of the wound in the method of gastrostomy.

Further another object of the present invention is to provide a pin used in the infection catheter kit.

An infection preventive cover according to the present invention comprises a long-and-slender flexible tubular sheath and a first engaging mechanism, the first engaging mechanism engaging an in-stomach remaining (staying) member of a distal end of a percutaneous endoscopic gastrostomy catheter which is disposed within the tubular sheath with a distal end portion of the tubular sheath.

The infection preventive cover is longer than the distance from the stomach to mouth of a patient and has an enough length to entirely cover a percutaneous endoscopic gastrostomy catheter (PEG catheter). For the infection preventive cover (a flexible tubular sheath) there is favorably employed such materials which can maintain a state in which the infection preventive cover always encloses the PEG catheter (it hardly shrinks, or is hardly rumpled) even an external force is applied to the infection preventive cover in a longitudinal direction thereof, and which is airtight, waterproof, flexible and strong. Example of the materials are vinyl and rubber. The tubular sheath has such inner diameter that a tube of the PEG catheter loosely passes therethrough. The flexible tubular sheath can also be expressed as a flexible tube (member) in view of its shape of long and slender.

The first engaging mechanism included in the infection preventive cover is, in view of its function, for preventing the PEG catheter from being relatively shifted toward the top end of the tubular sheath or for preventing the tubular sheath from being relatively shifted toward to the distal end of the PEG catheter in relative positional relation between the PEG catheter and the tubular sheath.

In one embodiment of the present invention, the first engaging mechanism includes a first engaging member provided on the distal end portion of the tubular sheath, and the in-stomach remaining member is fixed to the distal end portion of the tubular sheath by being engaged with the first engaging member. The first engaging member is, for example, a pin (a first pin). The in-stomach remaining member is fixed to the distal end portion of the tubular sheath by being engaged with the pin which penetrates a circumferential wall of the distal end portion of the tubular sheath in a radial direction thereof. The tubular sheath is formed with holes, into which the first pin is inserted in a radial direction, on a circumferential wall of the distal end portion thereof. The in-stomach remaining member is fixed to the distal end portion of the tubular sheath by being engaged with the first pin inserted into the first holes. In the embodiment in which the in-stomach remaining member is engaged with a pin, preferably, the in-stomach remaining member includes a ring shaped member (portion) or a loop portion. The in-stomach remaining member is typically stays in a stomach. However it includes one which remains in the other hollow internal organs.

The infection preventive cover in accordance with the present invention is used in a method of gastrostomy as follows;

In the method of gastrostomy a guide wire is inserted into a stomach through an outer tube pierced through a wall of an abdomen and a wall of the stomach of a patient. The guide wire is pulled through an esophagus and an oral cavity into a space outside the patient. In this state, a distal end of the guide wire is maintained outside the outer tube. A top end of the guide wire pulled outside the oral cavity of the patient is joined with a top end (a conical top portion) of a percutaneous endoscopic gastrostomy (PEG) catheter. The PEG catheter is delivered from the mouth (oral cavity) into the stomach of the patient by pulling ("pulling method") or pushing ("pushing method") the guide wire in a state where the catheter is enclosed with an infection preventive cover.

Prior to the delivery of the PEG catheter into the stomach from the mouth of the patient, the PEG catheter is entirely enclosed with the infection preventive cover including the long-and-slender tubular sheath and an in-stomach remaining member provided at a distal end of the PEG catheter is fixed to a distal end portion of the infection preventive cover (tubular sheath) using a first engaging mechanism. The catheter may be inserted into the tubular sheath when the infection preventive cover or the PEG catheter is manufactured, or alternatively the PEG catheter may be inserted into the tubular sheath in or before the performance of an operation.

After the PEG catheter is delivered through the oral cavity into the stomach with the PEG catheter covered with the infection preventive cover, the in-stomach remaining member is released from the distal end portion of the infection preventive cover in a space outside the oral cavity, and further the guide wire is drawn into a space outside the body of the patient (for example, by pulling the distal end of the guide wire). The PEG catheter is drawn through the top end of the tubular sheath in the stomach. The PEG catheter is drawn through the stomach wall and the abdomen wall (wound) into a space outside the patient together with the outer tube. Thereafter the infection preventive cover is removed from the oral cavity into a space outside the patient. The in-stomach remaining member at the distal end of the PEG catheter is left in the stomach (inclusive of a case where the in-stomach remaining member is cut off from the tube of the PEG catheter).

In accordance with the present invention, the PEG catheter (and, in some cases, the joint section between the PEG catheter and the guide wire in dependence upon the construction of the PEG catheter) is covered outside the oral cavity with the infection preventive cover having a tubular sheath to be delivered from the oral cavity into the stomach in the covered state. Since the in-stomach remaining member at the distal end of the PEG catheter is fixed to the distal end of the tubular sheath, the PEG catheter is delivered into the stomach in the covered state, when the PEG catheter is drawn by pulling the guide wire. The catheter does not directly brought into contact with the oral cavity, the larynx and the upper pharynx of the patient. The catheter is therefore kept clean.

The PEG catheter is withdrawn through the top end of the infection preventive cover in the stomach and is drawn through a hole (wounded part of the patient) prepared in the abdominal and stomach walls into a space outside the patient. When the PEG catheter is delivered into the stomach, the catheter is kept clean, namely, is not inflected. Even when the clean PEG catheter is brought into contact with the hole (wound) in the abdominal and stomach walls, the hole (wound) is hardly inflected. Consequently, infection of the wound can be efficiently prevented.

Preferably, the tubular sheath is provided with a closing film covering an opening at the top end thereof. The top end of the PEG catheter is prevented from being brought into contact with the oral cavity and so on, and such an effect is enhanced that bacteria are prevented from invading through the top end of the infection preventive cover. The closing film may be formed with a slit or a pin hole. When the top end of the guide wire is jointed with the top end of the PEG catheter after the PEG catheter is covered with the infection preventive cover, the top end of the guide wire can be inserted into the infection preventive cover from the top end thereof through the slit or the pin hole.

More preferably, the infection preventive cover further comprises a second engaging mechanism. The second engaging mechanism fixes the top end of the guide wire, which is inserted into the top end of the PEG catheter disposed inside of the tubular sheath, passes therethrough and appears outside of the PEG catheter at the distal end thereof, to the distal end portion of the tubular sheath. When the infection preventive cover having the second engaging mechanism is used, the guide wire is inserted into the PEG catheter (tube), passes therethrough and appears outside of the PEG catheter at the distal end thereof. The top end of the guide wire appearing outside is fixed to the distal end portion of the tubular sheath by the second engaging mechanism. The first engaging mechanism and the second engaging mechanism may be realized by one and common engaging mechanism.

In one embodiment, the second engaging mechanism includes a second engaging member provided on the distal end portion of the tubular sheath. The top end of the guide wire is fixed to the distal end portion of the tubular sheath with a head portion, a hook portion or a ring or loop portion of the top end of the guide wire being engaged with the second engaging member. The second engaging member is, for example, a pin (a second pin) penetrating the circumferential wall of the distal end portion of the tubular sheath in a radial direction thereof. The second pin is formed with a wide slit section allowing a large diameter head formed at the top end of the guide wire to pass therethrough and a narrow slit section formed continuous with the wide slit section and preventing the head from passing therethrough. The top end of the guide wire is fixed to the distal end portion of the tubular sheath with the head of the guide wire which has passed through the wide slit section being engaged with the second pin at the narrow slit section. The large diameter head means that a diameter of the head is larger than that of the guide wire (except for the head portion). One pin may be used as both the first pin and the second pin. In a case where the second pin which is prepared separately from the first pin is used, second pin holes for inserting the second pin is formed on the circumferential wall of the distal end portion of the tubular sheath in a radial direction in addition to the first pin holes, and the second pin is inserted into the second pin holes. The guide wire is formed with a hook at the top end thereof in place of the large diameter head. A ring or loop may be formed using part of or whole of the wire guide by bending or holding the guide wire double.

A method of gastrostomy using an infection preventive cover which has a first and second engaging mechanisms comprises the steps of inserting a guide wire into a stomach through an outer tube pierced through a wall of an abdomen and a wall of the stomach of a patient, pulling the guide wire through an esophagus and an oral cavity into a space outside the patient, inserting the guide wire into the inside of a percutaneous endoscopic gastrostomy (PEG) catheter which is entirely enclosed with an infection preventive cover having a long-and-slender flexible tubular sheath through a top end thereof, and engaging a top end of the guide wire which appears from a distal end of the PEG catheter with a distal end portion of the infection preventive cover (engagement or fixing using the second engaging mechanism).

The method further comprises the steps of engaging an in-stomach remaining member of a distal end of the PEG catheter with a distal end portion of the infection preventive cover (engagement or fixing using the first engaging mechanism), and delivering the PEG catheter through the oral cavity into the stomach by pulling or pushing the guide wire with the PEG catheter covered with the infection preventive cover.

The method further comprises the steps of releasing the top end of the guide wire from the distal end portion of the infection preventive cover, and releasing the in-stomach remaining member from the distal end portion of the infection preventive cover in a space outside the oral cavity. By pulling the guide wire into a space outside the patient, the top end of the guide wire moves through the PEG catheter (PEG tube) toward the top end thereof. The top end of the guide wire is automatically joined with the top end portion of the catheter in the stomach.

The method finally comprises the steps of drawing the catheter into the space outside the patient by further pulling the guide wire into the space outside the patient, while drawing the PEG catheter through the top end of the tubular sheath, and removing thereafter the infection preventive cover from the oral cavity into a space outside the patient.

Since the top end of the guide wire is fixed to the distal end of the infection preventive cover, the pulling force acting on the guide wire is transmitted to the distal end portion of the infection preventive cover, when the PEG catheter is delivered into the stomach. The top end of the catheter is surely prevented from appearing outside from the top end of the infection preventive cover, when the PEG catheter is delivered into the stomach.

A common pin may be used in the first and second engaging mechanisms. In this case, the pin is drawn from the distal end portion of the infection preventive cover, then the top end of the guide wire is released from the distal end portion of the infection preventive cover and the in-stomach remaining member is also released from the distal end potion of the infection preventive cover.

An infection preventive catheter kit according to the present invention comprises a infection preventive cover and a percutaneous endoscopic gastrostomy (PEG) catheter. The infection preventive cover includes a long-and-slender flexible tubular sheath (flexible tube), and a first engaging mechanism for engaging an in-stomach remaining member provided on a distal end of the PEG catheter which is disposed inside of the tubular sheath with the distal end portion of the tubular sheath. The in-stomach remaining member of the catheter has a portion subjected to engagement by the first engaging mechanism. This infection preventive catheter kit is offered as a combination of the infection preventive cover and the percutaneous endoscopic gastrostomy catheter. It is sufficient to enclose the PEG catheter with the infection preventive cover before performing the operation or during the operation, that is, to insert the PEG catheter into the infection preventive cover. Of course, the PEG catheter may be covered with the infection preventive cover in the manufacturing stage.

The infection is prevented by using the infection preventive catheter kit in the method of gastrostomy.

In one embodiment, the first engaging mechanism includes a first pin penetrating radially the circumferential wall of the distal end portion of the tubular sheath, and the engagement portion of the in-stomach remaining member is a ring or loop member which can be engaged with the pin. Since a part of the in-stomach remaining member is formed to be the ring or loop, the in-stomach remaining member is fixed to the distal end portion of the tubular sheath by being engaged with the pin which penetrates radially the circumferential wall of the distal end portion of the tubular sheath.

The present invention further provide a pin used in the above infection preventive catheter kit. This pin is formed with a wide slit section allowing a large diameter head formed at a top end of a guide wire to pass thereghrough and a narrow slit section formed continuous with the wide slit section and preventing the head from passing therethrough. When this pin is used in the method of gastrostomy, the in-stomach remaining member provided at the distal end of the percutaneous endoscopic gastrostomy (PEG) catheter is engaged with the distal end of the infection preventive cover, and the large diameter head formed at the top end of the guide wire is engaged with the distal end portion of the infection preventive cover.

In one embodiment, the wide slit section is formed so as to penetrate the pin in a radial direction thereof and the width thereof continuously varies from one edge of the slit to the other edge (i.e., in a radial direction) to form a taper. That is, the width of one opening of the slit is narrow and that of the other opening is wide. By determining the angular position of the pin such that the wide opening is directed to a direction opposite to a direction in which the guide wire progresses, the top head of the guide wire can smoothly pass the slit of the pin along the taper.

Preferably, the cross-section of the pin is an n-sided polygon (n≧3), or has a shape of a circular or ellipse lacking a part, and pin holes formed on the distal end portion of the tubular sheath each has a shape similar to the cross-section of the pin. The pin is inserted into the pin holes only at a predetermined angular position. The pin does not rotate in the pin holes, and the pin can be always situated in such attitude that the wide opening is directed toward the top end of the progressing guide wire. The n-sided polygon includes a triangle, rectangle and other polygons. The definition that the pin hole has a shape similar to the cross-section of the pin includes the states that a gap between the pin hole and the pin is hardly found when the pin is inserted into the pin hole.

The present invention further provides a percutaneous endoscopic gastrostomy (PEG) catheter. The percutaneous endoscopic gastrostomy catheter has a PEG tube, a conical shaped top portion provided at a top of the PEG tube and an in-stomach remaining member provided at a distal end of the PEG tube, wherein the conical top portion is hollow and has an opening formed at the top end thereof, the opening has such size that a large diameter head formed at a top end of a guide wire passes therethrough, the inside diameter of the hollow space in the conical top portion is larger than that of the top opening, the hollow conical top portion is provided with an engaging piece on the inside thereof, the engaging piece allowing the head of the guide wire which is inserted through the top opening to pass therethrough and preventing the head from being pulled out, and center of the hollow space of the conical top portion is deviate from a center of an inside space of a portion joined to the PEG tube. The engaging piece has a concept which includes a part or a portion formed integral with the conical shaped top portion and a piece.

There are following merits in using the above percutaneous endoscopic gastrostomy (PEG) catheter of the present invention in the method of gastrostomy. When the guide wire which is pulled through an esophagus and an oral cavity into a space outside the patient is joined with the top portion of the PEG catheter in the method of gastrostomy, the operator has only to insert the top end (head) of the guide wire into the top opening formed on the conical top portion. The head formed on the top end of the guide wire enters into the hollow inside of the conical top portion through the top opening. The guide wire and the head are prevented from being pulled out by the engaging piece. The engaging piece may be formed separately from or may be integral with the conical top portion. Thus the top portion of the guide wire is joined with the conical top portion of the catheter. Further the center of the hollow space of the conical top portion is deviated from the center of the inside space of the portion joined to the tube. Even when the guide wire is swung up and down or the guide wire is relaxed or slacked, the movement of the guide wire is limited by the wall defining the hollow space of the conical top portion, the guide wire is hardly released from the engaging piece.

In one embodiment, the engaging piece has a slope formed obliquely with respect to a direction of insertion of the guide wire in the hollow inside space of the conical top portion. The engaging piece is formed with a wide slit at the upper portion of the slope or above the slope, the wide slit allowing the head of the guide wire to pass (the wide slit has a concept including a space formed above the slope and in continuous with a narrow slit as illustrated in the embodiment), and is formed with the narrow slit having a width smaller than that of the head of the guide wire for preventing the head to pass.

When the guide wire is inserted into the conical top portion through the top opening, the head portion provided at the top end of the guide wire slides up the slope of the engaging piece and reaches the upper portion or above the slope. The head portion of the guide wire falls down into the wide slit which allows the head portion to pass. The guide wire (except for the head portion) falls down into the narrow slit formed on the slope. Even if the guide wire is pulled, the head portion is not drawn out of the engaging piece. The guide wire and the PEG catheter are easily joined with each other, so that the operation is completed in a short time. Further the guide wire can be withdrawn to the distal end of the PEG catheter through the PEG catheter. The top end of the guide wire which appears from a distal end of the PEG catheter is fixed to a distal end portion of the infection preventive cover (tubular sheath) as described above. When the top end of the guide wire is released from the distal end portion of the infection preventive cover, and drawn toward the top end thereof, the top end of the guide wire is automatically joined with the top end portion of the catheter. The large head portion may not formed at the top end of the guide wire, but the guide wire may be folded double. In this case, the top portion of the PEG catheter is provided with a pin which passes through the doubled guide wire, so that the guide wire and the top end of the PEG catheter may be joined with each other.

Preferably, the center of the hollow space of the conical top portion is positioned at a lower part of the oblique engaging piece. Even when the guide wire is pulled, the head portion of the guide wire is surely engaged with the lower part of the engaging piece so that the guide wire is prevented from jumping out of the upper part of or above the engaging piece.

BRIEF DESCRIPTION OF THE DRAWINGS

The objects and features of the present invention will become more apparent from the consideration of the following detailed description taken in conjunction with the accompanying drawings in which:

FIG. 12 is a cross-sectional view schematically showing an enlarged part of a stomach of a patient in which a PEG catheter covered with an infection preventive cover is pulled in a PEG process;

FIG. 13 is a cross-sectional view schematically showing an enlarged part of a stomach of a patient in which a PEG catheter is drawn out of a body in a PEG process;

FIG. 14 is a cross-sectional view schematically showing a part of a stomach of a patient in which an in-stomach remaining member provided on a distal end of a PEG catheter passes through a PEG tube in a PEG process;

FIG. 15 is a cross-sectional view schematically showing a part of a stomach of a patient in which an in-stomach remaining member provided on a distal end of a PEG catheter abuts on a stomach wall in a PEG process;

DESCRIPTION OF THE PREFERRED EMBODIMENTS

Figure 1:
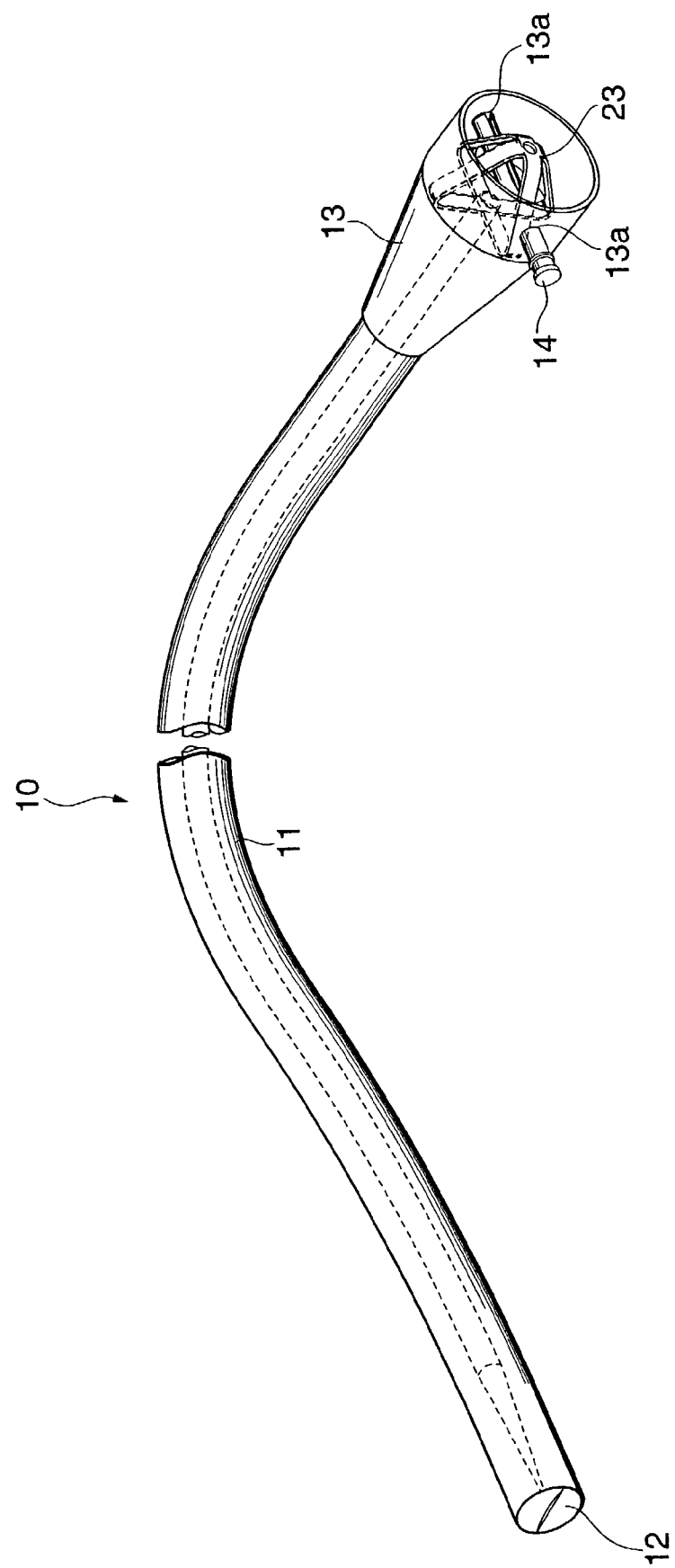
FIG. 1 is a perspective view of an infection preventive cover.
Figure 2:
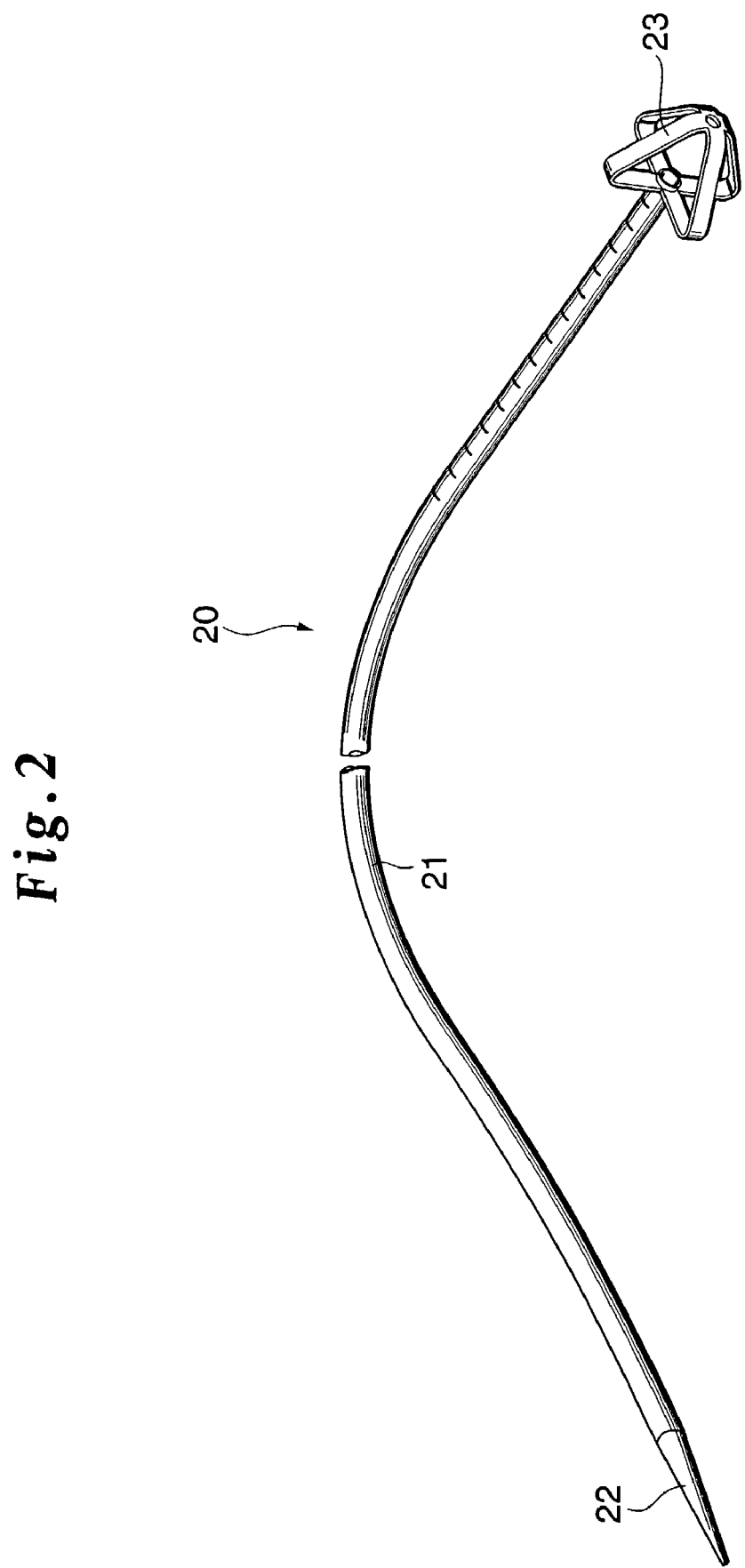
FIG. 2 is a perspective view of a PEG catheter.

FIG. 1 shows an infection preventive cover used in a percutaneous endoscopic gastrostomy (referred to as a "PEG"). FIG. 2 shows a gastrostomy catheter (referred to as a "PEG catheter").

The infection preventive cover 10 is used to enclose or cover the PEG catheter 20 (a PEG tube 21, a tapered portion 22 and an in-stomach remaining (staying) member or device 23) in its entirety to prevent the PEG catheter 20 from being infected in the oral cavity, the upper pharynx or the larynx. The infection preventive cover 10 comprises a long, slender, hollow and flexible tubular sheath 11. In other words, the flexible tubular sheath is called a flexible tubular body or a flexible tube. The flexible tubular sheath 11 is provided with a thin top film 12 covering or closing a top end opening of the tubular sheath and fixed to the top end of the tubular sheath, the film 12 being formed with a slit. The flexible tubular sheath 11 is provided with a hollow socket 13 formed integrally therewith at a distal end thereof. The socked 13 comprises a substantially hollow circular truncated conical portion and a substantially circular cylindrical portion formed continuously to an end of the conical portion having a larger opening. Another end of the socket 13 having a smaller opening is fixed (e.g., adhered, molten or melted) to the distal end of the tubular sheath 11 using, for example, an adhesive, or the socket 13 and the tubular sheath 11 are integrally formed with each other. The socket 13 is formed with two holes 13a for receiving a pin 14 on the circular cylindrical portion at opposite points (positions of point symmetry with respect to a center). The pin 14 inserted into the holes 13a is used to engage a top end portion of a guide wire and the in-stomach remaining member 23 provided on a distal end of the PEG catheter 20 at a position of the socket 13 of the infection preventive cover 10, as described later, the guide wire being used for delivering the PEG catheter 20 into a body of a patient in a state where the PEG catheter 20 is enclosed within the infection preventive cover 10.

The tubular sheath 11 is made of an airtight, waterproof, flexible and strong material such as vinyl or a rubber, which is hardly shrunken. The tubular sheath 11 is preferably of a circular cylindrical shaped, but may be one having a flat cross-section (e.g., ellipse). The socket 13 is made of a hard material such as polycarbonate. The top film 12 is made of a thin sheet such as vinyl.

The PEG catheter 20 comprises the long-and-slender hollow PEG tube 21, the top tapered portion (or member) 22 and the in-stomach remaining (staying) member 23 provided at the distal end of the PEG tube 21, which are continuously coupled or joined with each other. The PEG tube 21 is made of an elastic material such as vinyl or a rubber. The tapered portion 22 is made of a relatively hard material such as polypropylene. The in-stomach remaining member 23 is made of a flexible and elastic material such as a silicone, which has a nature that it changes in shape when an external force is applied thereto but returns to an original shape when the external force is removed.

The infection preventive cover 10 has a length (the total length of the tubular sheath 11 and the socket 13) is slightly greater than that of the PEG catheter 20 (the total length of the tapered portion 22, the PEG tube 21 and the in-stomach remaining member 23). The inner diameter of the tubular sheath 11 is greater than the outer diameter of the PEG tube 21, but is smaller than the diameter or width of the in-stomach remaining member 23 provided on the distal end of the PEG catheter 20. The inner diameter of the tubular sheath 11 may be greater than that of the in-stomach remaining member 23 in dependence upon the material for the in-stomach remaining member 23. In any way, it is sufficient that the PEG catheter 20 including the in-stomach remaining member 23 (in the state where the member is folded, or in its original shape) passes through the tubular sheath 11. It is desirable that a lubricant such as a lubricant jerry is applied on an inner surface of the tubular sheath 11.

Referring now to FIGS. 3 to 15, description will be given in detail of a usage method and a role of the infection preventive cover 10 configured above in relation to the PEG method. In this example, a method called "pull method (techniques)" will be described. The PEG method is performed in general by an operator, an endoscopist and one or two nurses.

Figure 3:
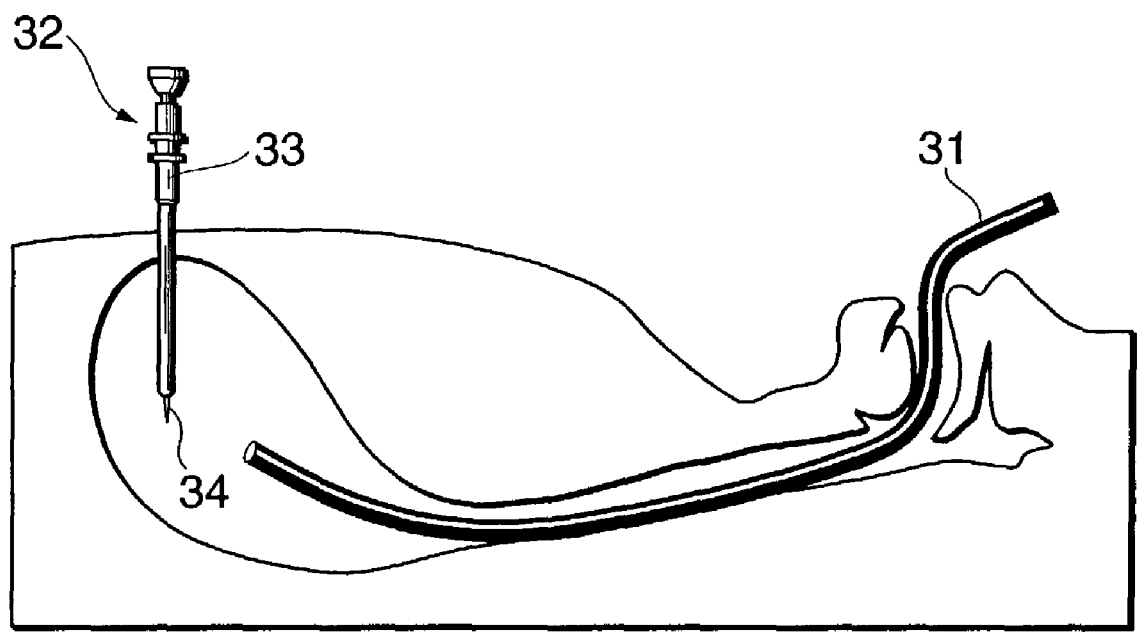
FIG. 3 is a cross-sectional view schematically showing an upper half of a body of a patient in which a endoscope is inserted in the body in a PEG process.

An endoscope 31 is inserted from a mouth of a patient in a supine position into her or his stomach. Air is fed through the endoscope 31 into the stomach of the patient to expand the stomach to resultantly tightly fix the stomach wall onto a peritoneum of the patient. A puncturing part is determined and its peripheral is completely disinfected. After the periphery is locally anesthetized, about one centimeter of skin is incised in the puncturing part and then needle 32 with an outer tube is pierced thereinto (FIG. 3).

The needle 32 includes an outer tube (pipe) 33 of a cylindrical contour and a needle (inner tube) 34 having a sharp end. The outer tube 33 is hollow. With the needle 34 completely installed in the external tube 33, the sharp end of the needle 34 is projected from an end of the outer tube 33. The sharp end of the needle 34 thrusts into the abdomen wall, the peritoneum and the stomach wall, and the outer tube 33 also passes through the abdomen wall, the peritoneum and the stomach wall.

Figure 4:
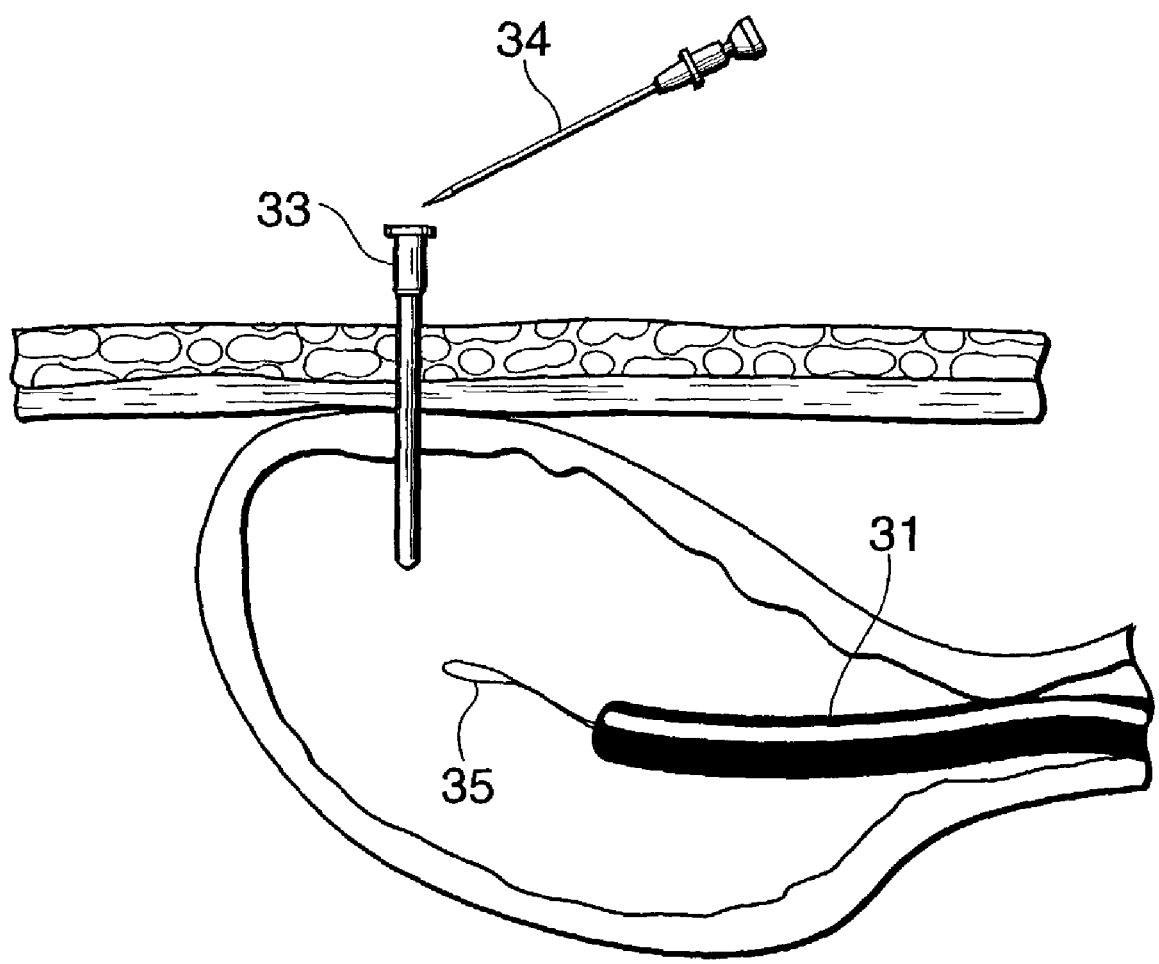
FIG. 4 is a cross-sectional view schematically showing an enlarged part of a stomach of a patient in which a endoscope is inserted in the body in a PEG process.

The needle 34 is removed from the outer tube 33. The outer tube 33 is kept pierced ranging from the abdomen wall to the stomach wall. An end of a snare forceps 35 is drawn from an end of the endoscope 31 to be exposed in the stomach (FIG. 4).

Figure 5:
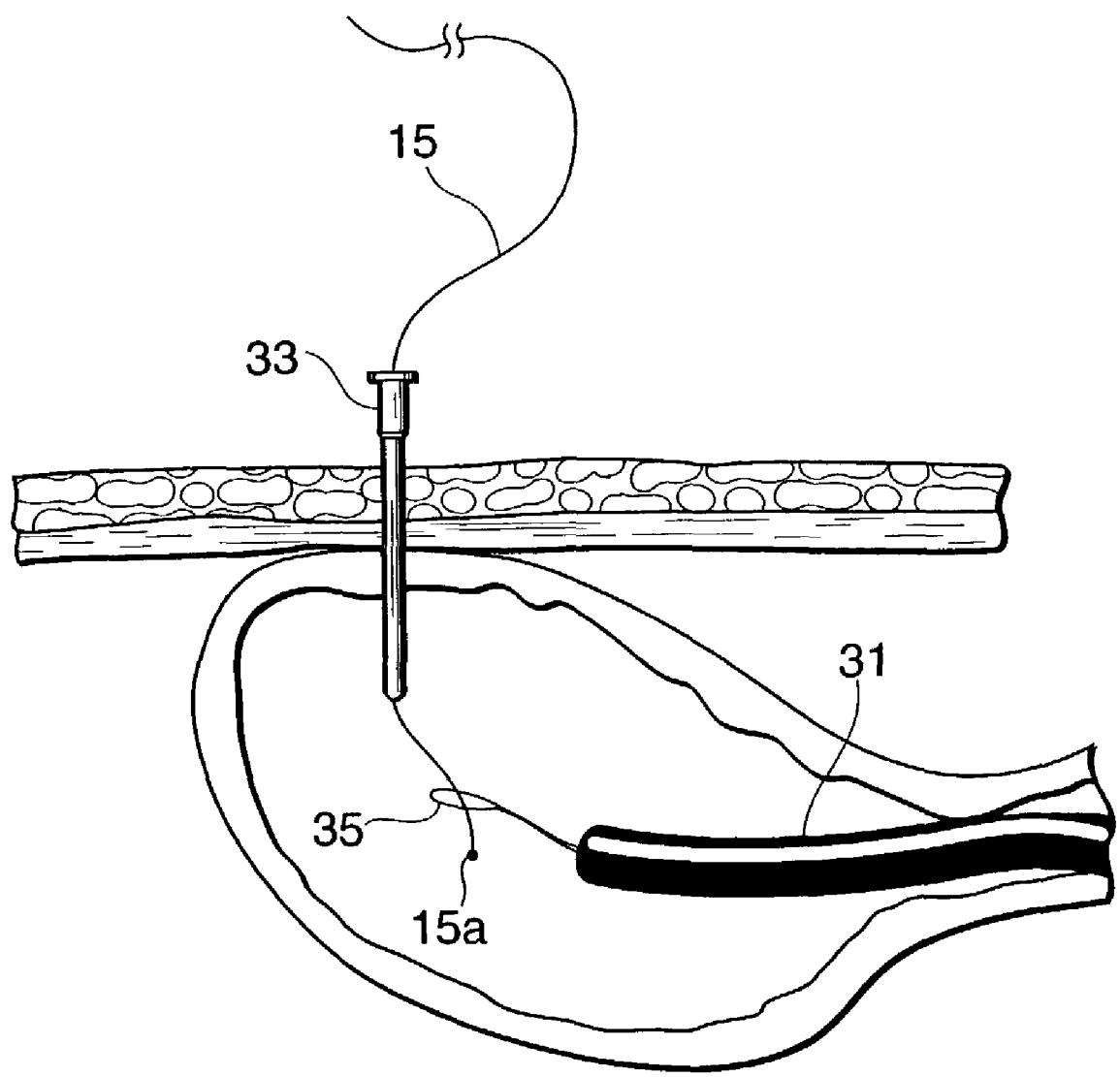
FIG. 5 is a cross-sectional view schematically showing a part of a stomach of a patient in which a guide wire is inserted into the stomach in a PEG process.
Figure 6:
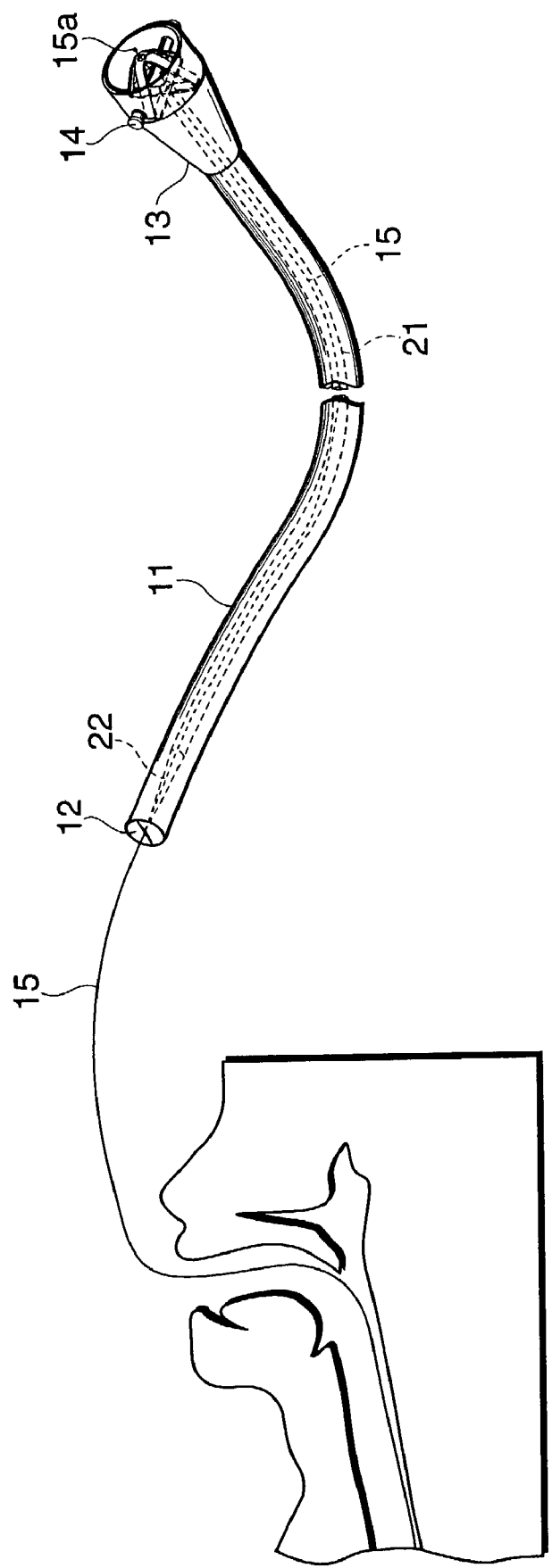
FIG. 6 is a perspective view showing a state in which a guide wire is engaged with a portion of a socket of an infection preventive cover in a PEG process.

A guide wire 15 having a spherical head 15a at a top end thereof is passed through the outer tube 22 to be inserted into the stomach (FIG. 5).

A top end portion of the guide wire 15 fed into the stomach is grasped by the snare forceps 35. The guide wire 15 held by the snare forceps 35 is withdrawn out of the oral cavity of the patient together with the endoscope 31. After the guide wire 15 is sufficiently drawn out of the oral cavity, the guide wire 15 is released from the snare forceps 35. The distal end of the guide wire 15 is kept outside of the outer tube 33.

The PEG catheter 20 includes the PEG tube 21 which has a top end portion conically tapered (this portion is the tapered portion or member 22) and a distal end having the in-stomach remaining member 23 integrally formed therewith (see FIG. 2). The tapered portion 22 side end of the PEG catheter 20 is fed into the tubular sheath 11 through the opening of the socket 13 of the infection preventive cover 10 to cover or enclose the PEG catheter 20 entirely from the tapered portion 22 to the in-stomach remaining member 23 by or in the infection preventive cover 10 (see FIG. 1). The PEG catheter 20 is covered or enclosed with the infection preventive cover 10 on manufacturing it or before performing an operation.

The tapered portion 22 of the PEG catheter 20 is formed with an opening at a top end thereof, which is connected to the hollow inside of the PEG tube 21 as described later. The top end of the tapered portion 22 is moved or shifted such that the top end of the tapered portion 22 slightly appears outside from the top end film 12 provided at the top end of the tubular sheath 11 (the top end of the tapered portion 22 is not necessarily needed to appear from the top end film 12), and the top end of the guide wire 15 which has been withdrawn out of the oral cavity is fed into the PEG tube 21 through the opening of the tapered portion 22. The guide wire 15 is continued to be fed into the PEG tube 21, so that the top end of the guide wire 15 passes through the distal end of the PEG tube 21 and the in-stomach remaining member 23 to appear outside. The top head portion 15a of the guide wire 15 and the in-stomach remaining member 23 of the PEG tube 21 is fixed (engaged) at the position of the socket 13 by inserting the pin 14 into the holes 13a formed on the socket 13 of the infection preventive cover 10, as will be described next.

Figure 7A:
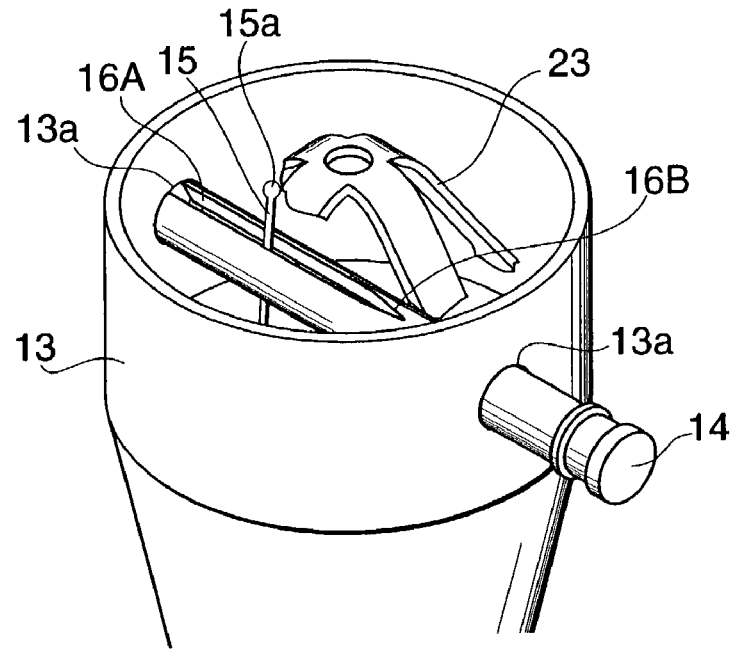
FIG. 7a and 7b are an enlarged perspective views showing a state in which a top end of a guide wire is engaged with a portion of a socket of an infection preventive cover.
Figure 7B:
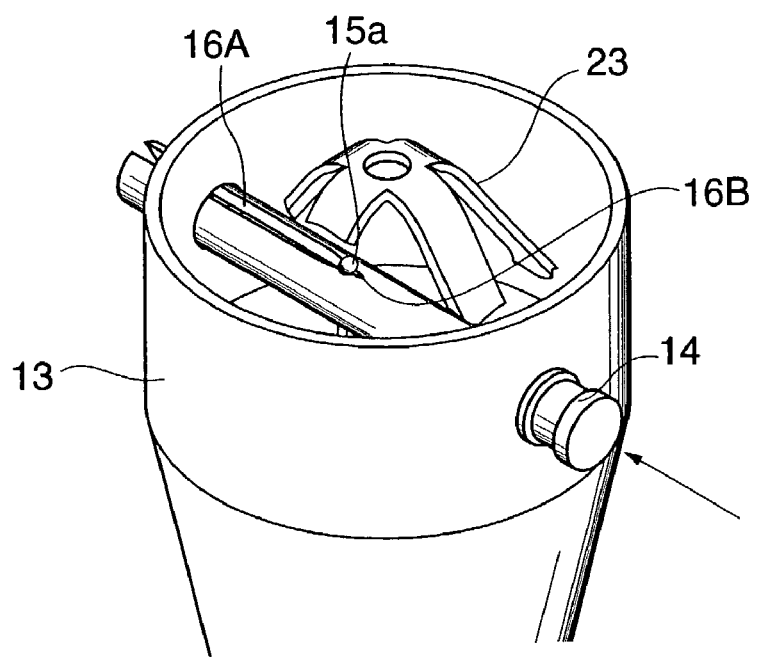
Figure 8:
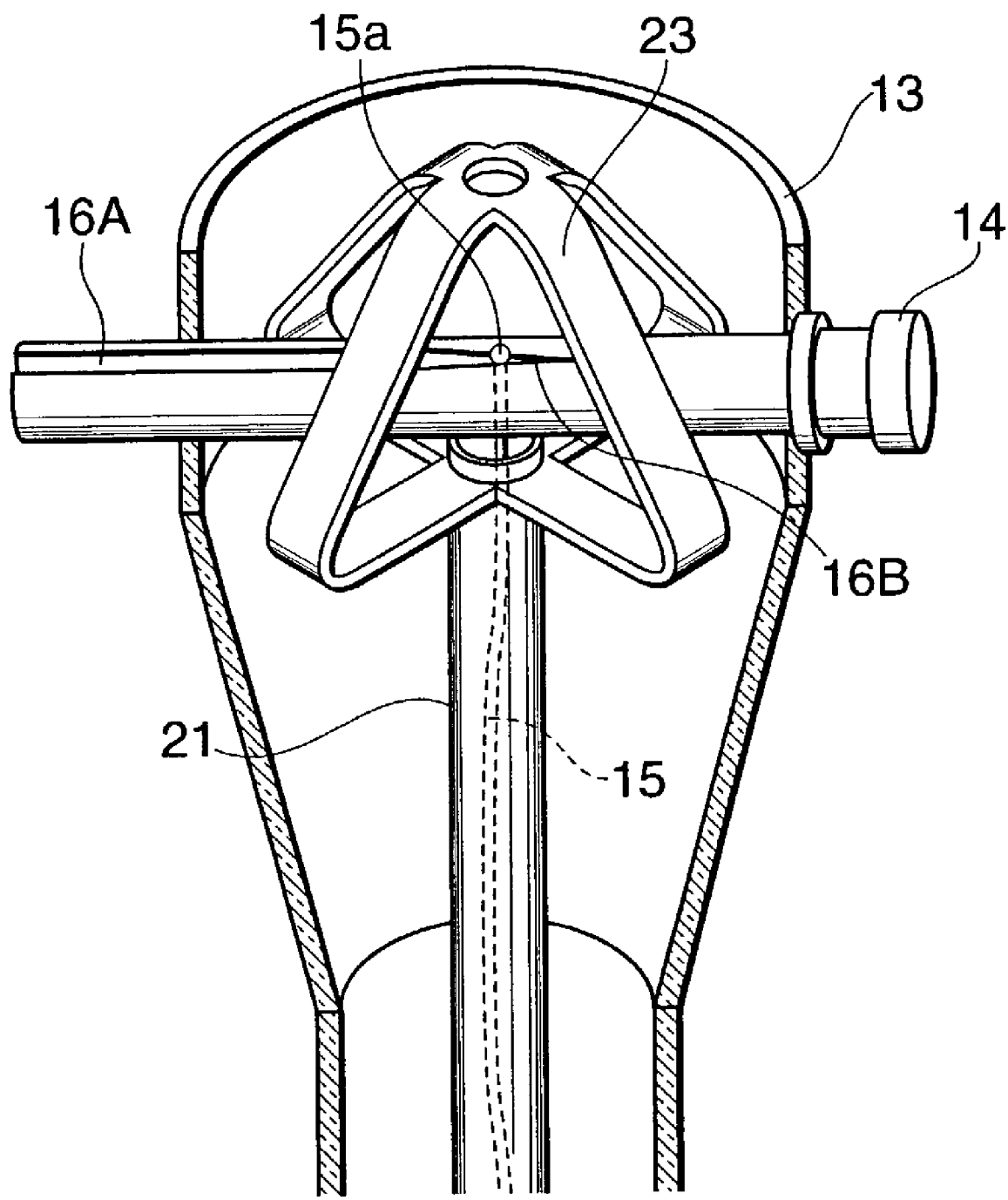
FIG. 8 is an enlarged perspective view showing a state in which an in-stomach remaining member provided on a distal end of a PEG catheter is engaged with a portion of a socket of an infection preventive cover.
Figure 9A:
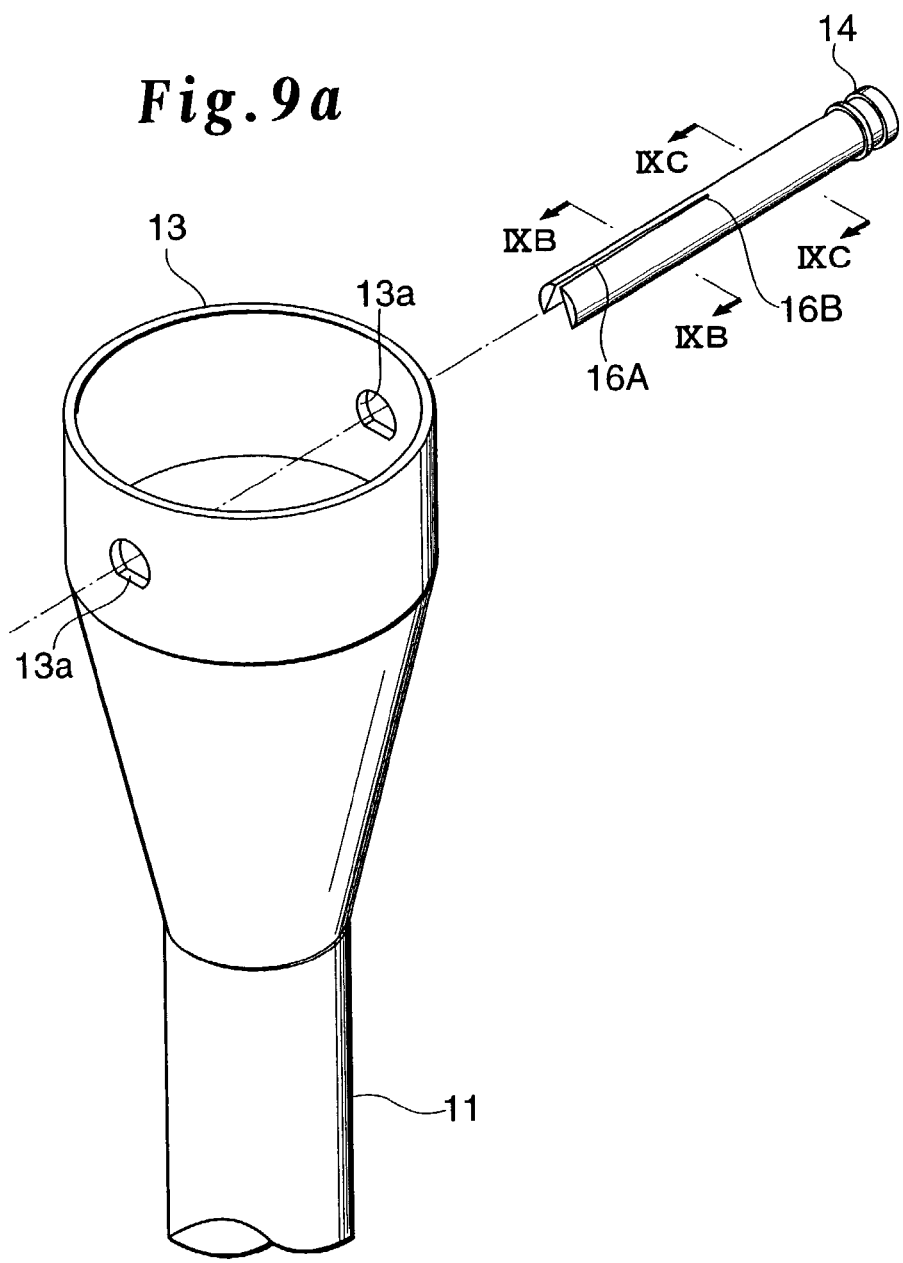
FIG. 9a is an enlarged perspective view showing a pin-receiving hole formed on a socket provided on a distal end of a infection preventive cover, and a pin inserted in the hole.
Figure 9B:
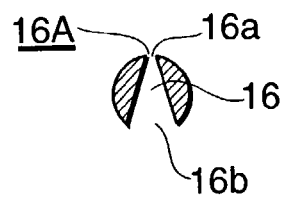
FIG. 9b is a cross-sectional view taken along the line IXB-IXB of a pin.
Figure 9C:
FIG. 9c is a cross-sectional view taken along the line IXC-IXC of a pin.

FIGS. 7a and 7b illustrate engagement of the guide wire 15 using the pin 14, and FIG. 8 illustrates engagement of the in-stomach remaining member 23 using the pin 14, FIG. 9a shows the shape of the pin 14 and the shape of the hole 13a which is formed on the socket 13 and into which the pin 14 is inserted. FIGS. 9b and 9c show cross-sectional views of the pin 14, where FIG. 9b is a cross-sectional view taken along the line IXB-IXB in FIG. 9a, and FIG. 9c is a cross-sectional view taken along the line IXC-IXC in FIG. 9a.

As shown in FIG. 9a, the socket 13 is formed with two pin holes 13a on the circumferential wall thereof at opposite positions, the pin hole 13a having a shape of a half circle at an upper side thereof (the side of an opening of the socket 13) and a shape of a straight line at a lower side thereof (the side of the tubular sheath 11). The pin 14 has a cross section corresponding to the shape of the hole 13a (a shape of a circle which is partly cut by a chord) (see FIG. 9c).

Accordingly, an angular position of the pin 14 inserted into the hole 13a is always predetermined and fixed. Namely, the circular circumferential surface of the pin 14 is always directed to the upper side (the side of the opening of the socket 13), and the flat surface of the pin 14 is always directed to the lower side (the side of the tubular sheath 11).

The pin 14 is formed with a slit 16 in the axial direction from one end (top end) thereof to a position around center thereof (the other end side). The slit 16 (mainly a wide slit section 16A described later) is tapered in the radial direction, where the slit width 16b on the flat surface side is wider than the slit width 16a on the circular circumferential surface side (see FIG. 9b).

As shown in FIG. 7a, the slit 16 formed on the pin 14 has a wide slit section 16A and a narrow slit section 16B formed continuous with the wide slit section 16A, the width of which gradually narrowed. The wide slit section 16A has a such width that the spherical head portion 15a formed at the top end of the guide wire 15 passes therethrough, and the narrow slit section 16B has a width which is smaller than the diameter of the head portion 15a of the guide wire 15. The guide wire 15 which has been fed into the PEG tube 21 and has appeared outside from the distal end of the PEG tube 21 passes through the wide slit section 16A (FIG. 7a). Since the slit width 16b on the lower side of the pin 14 is formed wider, the guide wire 15 smoothly passes the wide slit section 16A along the tapered surface. Thereafter the top end of the pin 14 is inserted into the hole 13a. The position of guide wire 15 relatively shifted to the narrow slit section 16B, so that the top head portion 15a is engaged with the narrow slit section 16B and the guide wire 15 is fixed. Even if the portion of the guide wire 15 which stays outside of the abdomen of the patient through the outer tube 33 is pulled into a space outside of the abdomen, the head 15a of the guide wire 15 is not fallen out of the pin 14 (FIG. 7b).

As shown in FIG. 8, the in-stomach remaining member 23 provided on the distal end of the PEG tube 21 comprises, in this embodiment, four flexible and bendable finger members which are combined so as to cross each other and linked or connected to or joined with each other at their top ends, and distal ends respectively. The four finger members are coupled to or joined with the distal end of the PEG tube 21 at their distal ends. Thus, the four finger members form a space (gap, ring, loop or engagement portion) through which the pin 14 passes through. The in-stomach remaining member 23 is engaged with the pin 14 inserted into the above space so that in-stomach remaining member 23 is fixed at a position of the socket 13. Even if the guide wire is pulled into a space outside of the abdomen of the patient, the PEG catheter 20 is not pulled out of the infection preventive cover 10.

Figure 10:
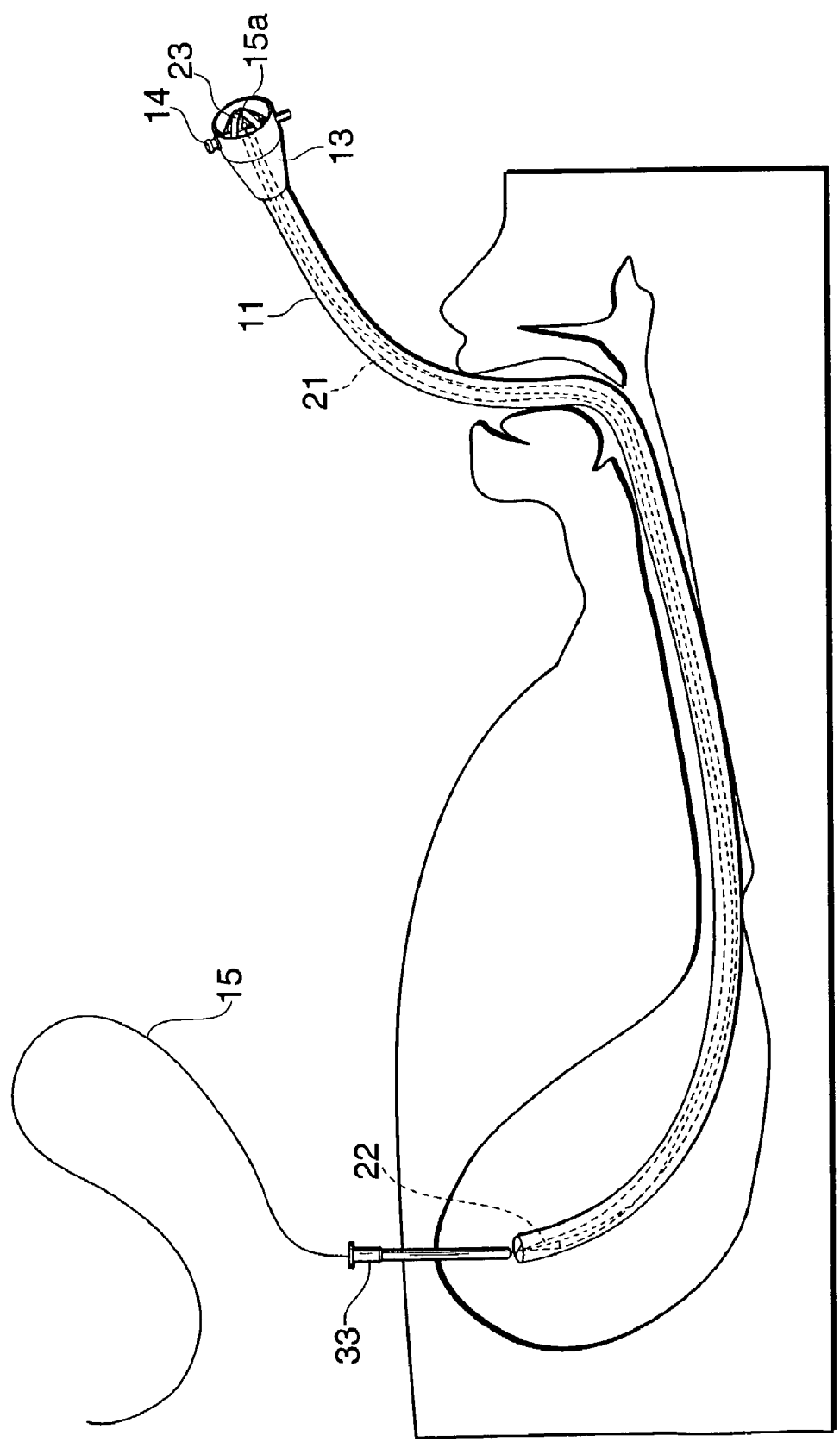
FIG. 10 is a cross-sectional view schematically showing an upper half of a body of a patient in which a PEG catheter covered with an infection preventive cover is pulled in a PEG process.

The end of the guide wire 15 drawn through the outer tube 33 into a space outside the body of the patient is pulled, in a state where the head portion 15a of the guide wire 15 and the in-stomach remaining member 23 are engaged with the pin 14 and fixed at the position of the socket 13. Since the top head portion 15a of the guide wire 15 is engaged with the pin 14, the pulling force acts on the pin 14. This causes the PEG tube 21 and infection preventive cover 10 to be delivered through the oral cavity, the upper pharynx and the larynx into the stomach with the tapered portion 22 and the PEG tube 21 covered with the infection preventive cover 10 (FIG. 10). The pushing force may be applied to the PEG tube 21 and infection preventive cover 10.

When the guide wire 15 is further drawn, the tapered portion 22 of the PEG catheter 20 abuts on or reaches near an end of the outer tube 33. It is favorable to confirm this event, i.e., the tapered portion 22 abuts on or reaches near the end of the outer tube 33 by the endoscope. In this state, the in-stomach remaining member 23 at the distal end of the PEG catheter 20 and the socket 13 at the distal end of the infection preventive cover 10 are still outside the mouth of the patient.

Figure 11:
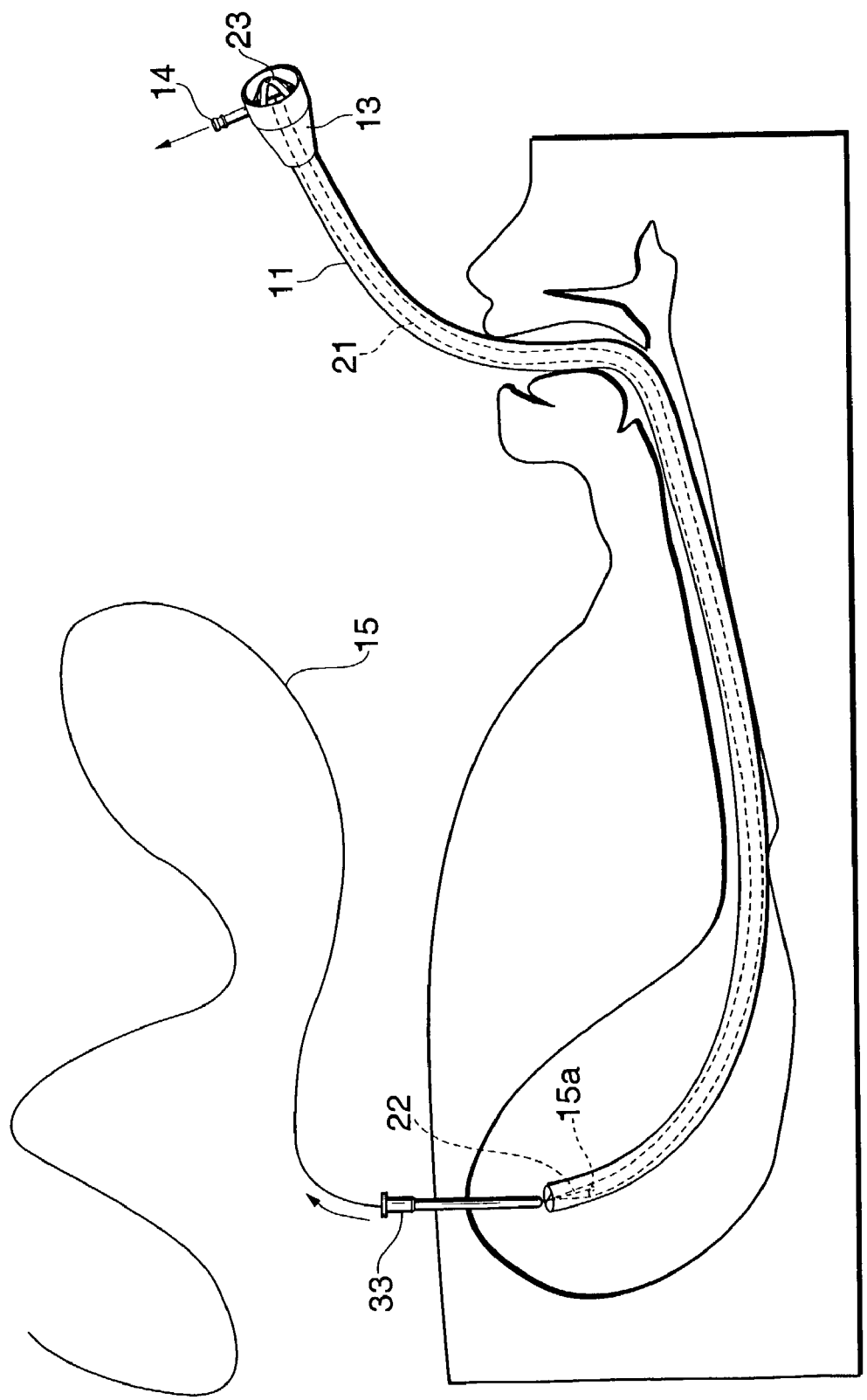
FIG. 11 is a cross-sectional view schematically showing an upper half of a body of a patient in which a PEG catheter covered with an infection preventive cover is pulled in a PEG process.

The pin 14 is drawn from the hole 13a halfway (a half of the whole length of the pin 14), and the engagement (lock) of the top head portion 15a of the guide wire 15 is released. After the head portion 15a is released from the pin 14, the guide wire 15 is further pulled into a space outside of the body of the patient, so that the top head portion 15a of the guide wire 15 passes through the wide slip section 16A of the pin 14 and is drawn toward the abdomen of the patient through the PEG tube 21. Finally, the spherical head portion 15a at the top of the guide wire 15 is fixed to (engaged with) an inner portion of the tapered portion 22 provided at the top of the PEG catheter 20 in the stomach, so that the guide wire 15 and the tapered portion 22 are automatically coupled together (linked or connected to or joined with each other) (FIGS. 11 and 12). The structure of the tapered portion 22 and the coupling structure will be described later in detail.

The pin 14 is drawn completely and the in-stomach remaining member 23 is released form the engagement. After the in-stomach remaining member 23 is released, the guide wire 15 is further withdrawn outwardly, while the outer tube 33 is being drawn through the stomach and abdomen walls. The tapered portion 22 connected to the guide wire 15 and the PEG tube 21 formed continuously to the tapered portion 22 are drawn through the film 12 at the top of the tubular sheath 11 to appear in a space inside the stomach of the patient. The flexible in-stomach remaining member 23 is drawn through the tubular sheath 11 in a folded state and moved toward the abdomen of the patient. While the guide wire is being withdrawn outside of the patient body, the socket 13 which is out of the patient in a mouth side of the patient is caught by the endoscopist etc. with his or her hand to prevent the infection preventive cover 10 from being drawn into the body of the patient. By further pulling or withdrawing the guide wire 15, the tapered portion 22 and the PEG tube 21 are delivered through the stomach wall and the abdomen wall into a space outside the patient body (FIGS. 13 and 14).

Finally, the in-stomach remaining member 23 appears in the stomach of the patient from the film 12 (which is broken) at the top of the tubular sheath 11, the four fingers are restored to their original shape, and the member 23 (four fingers) abuts on the stomach wall (FIG. 15). If necessary, this condition that the in-stomach remaining member 23 abuts on the stomach wall is confirmed by the endoscope 31. The tubular sheath 11 is removed from the mouth of the patient into a space outside the patient.

The PEG tube 21 thus withdrawn into a space outside the patient is cut at an appropriate point to have a necessary length, and the cut-off end is connected with an adapter (not shown) to supply a medicine for nutrition. The PEG tube 21 is attached onto the body of the patient with an appropriate fixing unit (means), thereby completing the operating of the PEG method.

The outer surfaces of the guide wire 15 and the tubular sheath 11 having passed through the larynx, the upper pharynx and the oral cavity are infected by bacteria on the oral cavity, the upper pharynx and the larynx. However, since the guide wire 15 is drawn through the outer tube 33 into a space outside the patient body, it hardly occurs that the wound (hole) in the stomach and abdomen walls is infected by the guide wire 15. Furthermore, the tapered portion 22, the PEG tube 21 and the in-stomach remaining member 23 are each covered with the tubular sheath 11 to be fed, in this state, through the oral cavity, the upper pharynx and the larynx into the stomach to be then withdrawn from the tubular sheath 11 through the film 12 in the stomach. The tapered portion 22 and the PEG tube 21 are covered by the tubular sheath 11 so that they are not infected by bacteria. Accordingly, when the tapered portion 22 and the PEG tube 21 are brought into contact with the wound when they are drawn to a space outside the patient, there is almost no chance that the wound is contaminated by bacteria. The tubular sheath 11 of which outer surfaces are infected are removed through the mouth of the patient. It does not occur that the wound is infected by the tubular sheath 11 (the infection preventive cover 10). In consequence, the infection of the wound can be advantageously prevented.

Also in the "push" method, it is possible to effectively prevent infection of the wound by pushing the PEG catheter 20 covered with the infection preventive cover 10 into the stomach.

Figure 16A:
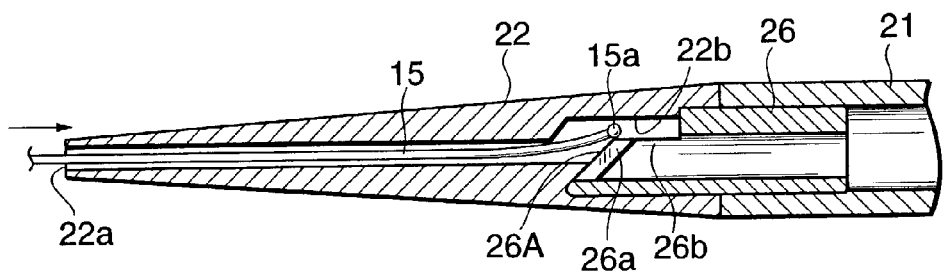
FIGS. 16a to 16c are cross-sectional views showing a state in which a guide wire is inserted into a PEG catheter through a top end thereof, FIG. 16a showing that a head portion of the guide wire slides up a slope of an engaging piece, FIG. 16b showing that the head portion of the guide wire is fallen down into a connecting member through a wide slit of the engaging piece, and FIG. 16c showing that the guide wire is further inserted.
Figure 16B:
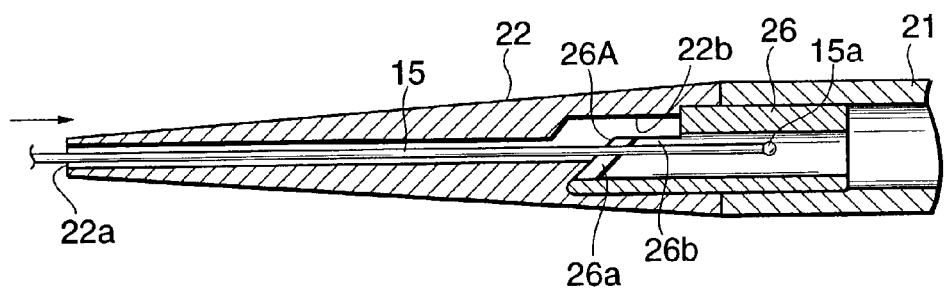
Figure 16C:
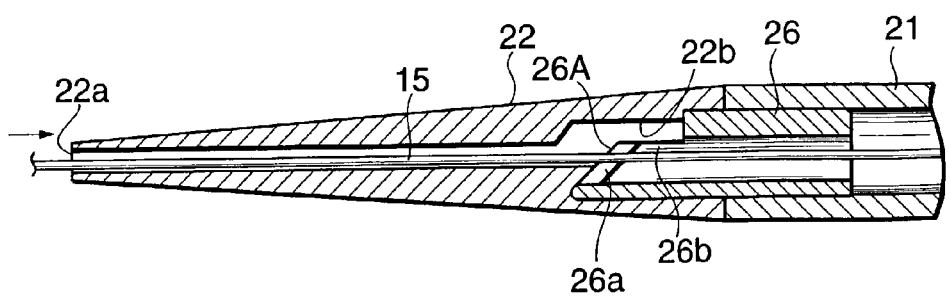
Figure 17A:
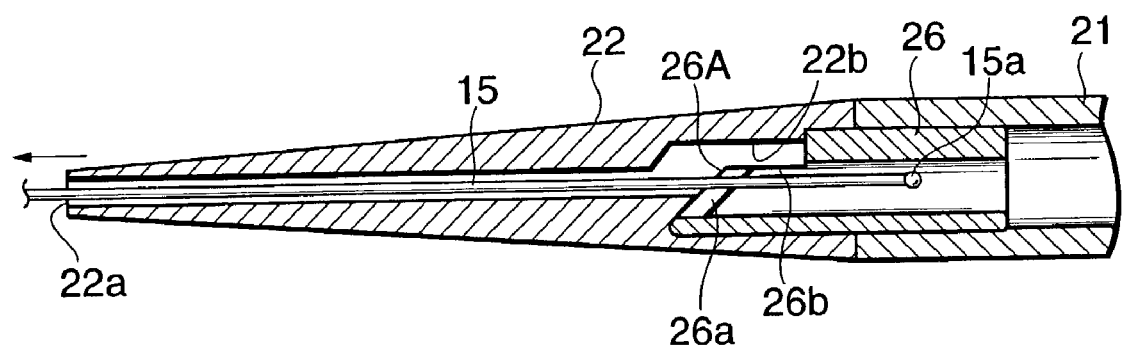
FIGS. 17a and 17b are cross-sectional views showing a state of joint of a head portion of a guide wire, FIG. 17a showing a state before the joining, and FIG. 17b showing that the head portion of a top of the guide wire is engaged with an engaging piece.
Figure 17B:
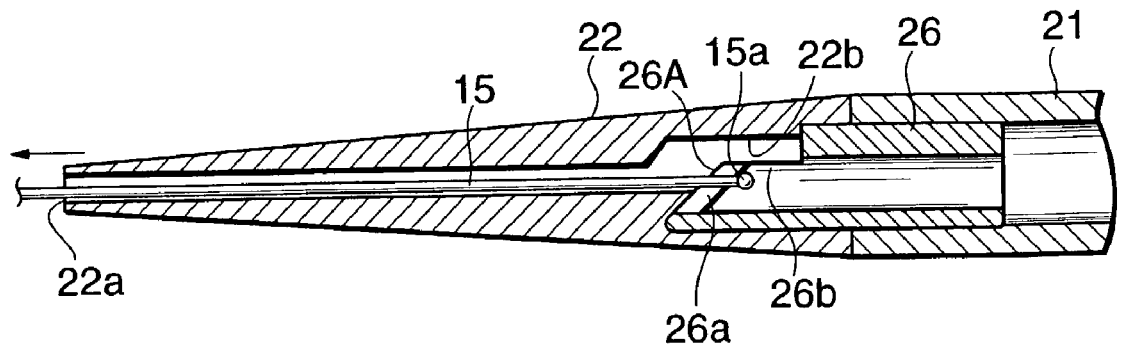
Figure 18A:
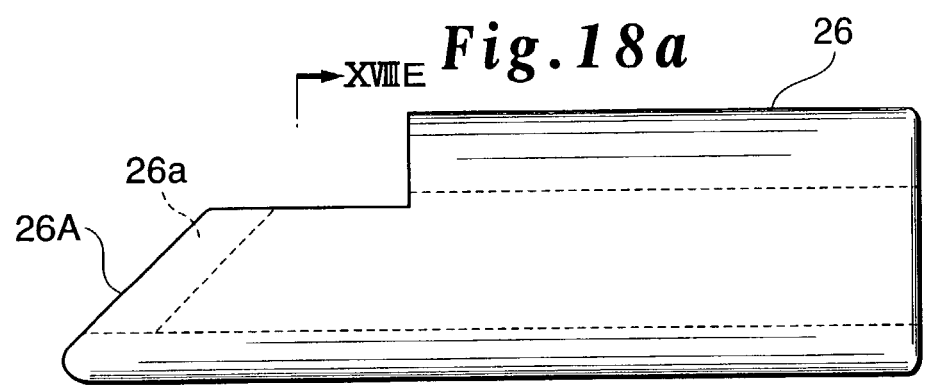
FIG. 18a is an enlarged side view of a connecting member constituting a tapered portion.
Figure 18B:
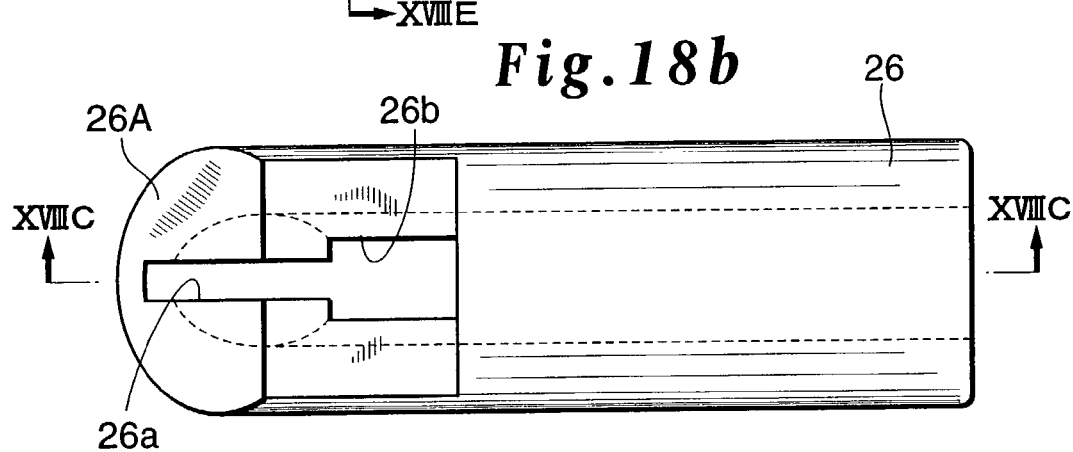
FIG. 18b is a plane view of the connecting member.
Figure 18C:
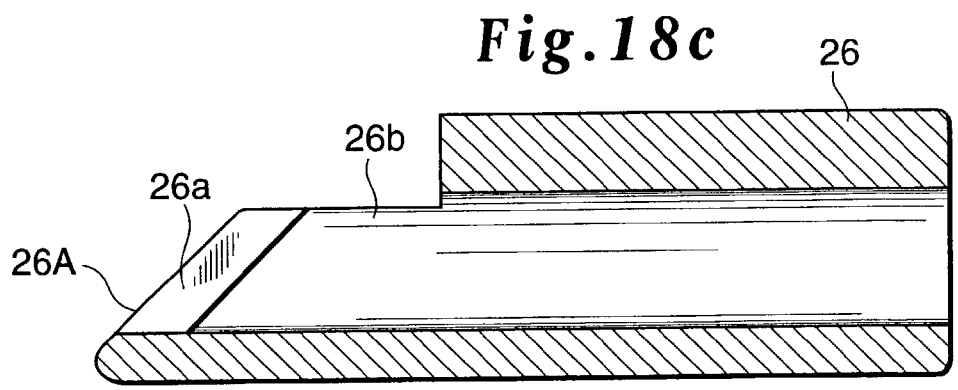
FIG. 18c is a cross-sectional view taken along the line XVIIIC-XVIIIC of the connecting member.
Figure 18D:
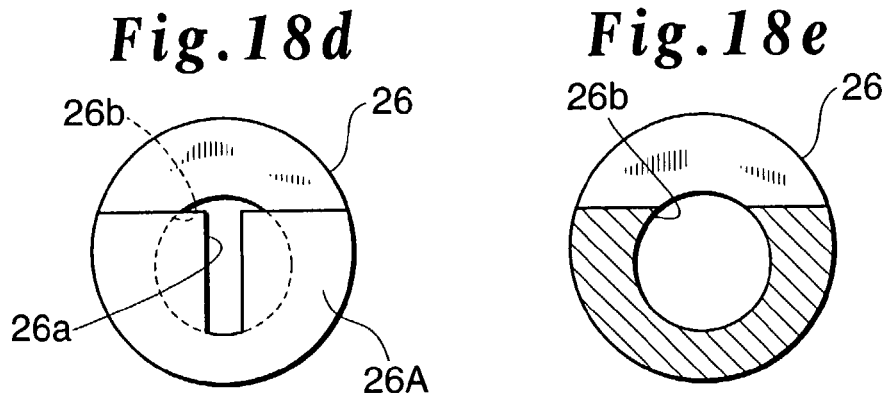
FIG. 18d is a front view of the connecting member.
Figure 18E:
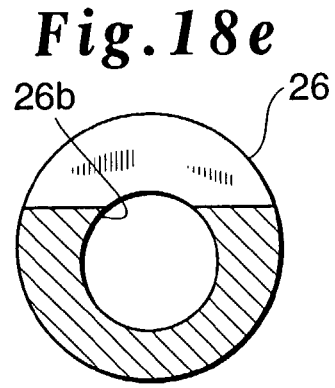
FIG. 18e is a cross-sectional view taken along the line XVIIIE-XVIIIE of the connecting member.
Figure 19:
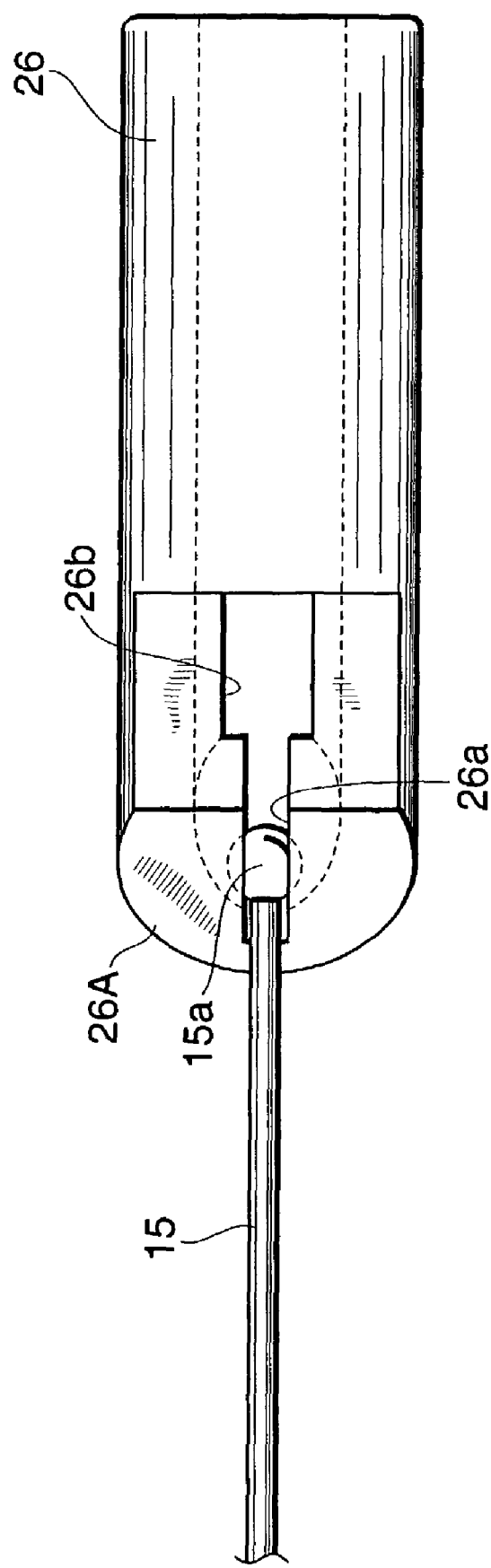
FIG. 19 is a plane view showing a state of joint between a guide wire and a connecting member.

FIGS. 16a to 16c illustrate a state where the guide wire 15 is inserted into the tapered portion 22 of the PEG catheter 20 at its top end. FIGS. 17a, 17b and 19 show connection or joint between the tapered portion 22 of the PEG catheter 20 and the guide wire 15 in the stomach of the patient in detail. FIG. 18a is an enlarged side view of a connecting member 26 which positions at a connecting (joint) portion of the tapered portion 22 and the PEG tube 21, FIG. 18b is an enlarged plane view of the connecting member 26, and FIG. 18c is an enlarged cross-sectional view taken along the line XVIIIC-XVIIIC of the connecting member 26. FIG. 18d is a front view of a top end of the connecting member 26, and FIG. 18e is a cross-sectional view taken along the line XVIIIE-XVIIIE of the connecting member 26.

The tapered portion (member) 22 at the top end of the PEG catheter 20 is of a substantially conical shaped, and is formed with a step at an inner side of a large diameter end portion thereof. The connecting member 26 is fitted into the step formed inside of the tapered portion 22. At the fitted portion, the tapered portion 22 and the connecting member 26 are fixed to each other by, for example, an adhesive or by molting. Thus the top end portion of the connecting member 26 positions inside of the tapered portion 22. The tapered portion 22, the connecting member 26 and the PEG tube 21 are fixed to each other by adhering or moltening the end surface of the tapered portion 22, the outer surface of the end portion of the connecting member 26 and the inner surface of the PEG tube 21. The connecting member 26 is hollow and has a cylindrical hole. The shape of the connecting member 26 is also substantially cylindrical (FIG. 18e).

The guide wire 15 which is drawn form the oral cavity of the patient is formed with a spherical shaped head 15a at the top end thereof, the diameter of which is larger than that of the guide wire 15. The tapered portion 22 of the PEG tube 21 is hollow (inside space is indicated by numerical reference 22b) and is formed with an opening (a hole) 22a at the top end thereof, the opening 22a allowing the head 15a to pass therethrough. The top end portion (including the head 15a) of the guide wire 15 which is drawn from the oral cavity is inserted into the inside of the tapered portion 22 through the opening 22a.

The connecting member 26 has a engaging piece (plate) 26A formed integrally therewith at the top end thereof (a portion positioned inside the tapered portion 22). The engaging piece 26 extends obliquely with respect to the axial direction of the connecting member 26 from the top end thereof, and then bent (formed) so as to be parallel with the axial direction (FIGS. 16a, 16b and 16c, FIGS. 17a and 17b). A portion of the engaging piece 26A which is oblique with respect to the axial direction is referred to as a "slope" (lower portion), and another portion of the engaging piece 26A which is paralleled with the axial direction is referred to as a "plane" (upper portion), hereinafter.

The engaging piece 26A is formed with a narrow slit 26a from the lower end of the slope to around the center of the plane (FIG. 18b). The engaging piece 26A is further formed with a wide slit 26b continuing the narrow slit 26a on the plane thereof, which allows the head portion 15a of the guide wire 15 to pass therethrough.

The tapered portion (member) 22 is formed with an upper space 22b inside thereof at the position where the engaging piece 26A is disposed, the space 22b allowing the head portion 15a of the guide wire 15 to pass (see FIGS. 16a, 16b and 16c, FIGS. 17a and 17b). When the guide wire 15 is inserted into the tapered portion 22 through the opening 22a at the top thereof, the spherical shaped head portion 15a formed at the top of the guide wire 15 slides up the slope of the engaging piece 26A and reaches the inner space 22b (above the plane of the engaging piece 26A) of the tapered portion 22 (FIG. 16a).

When the guide wire 15 is further inserted into the tapered portion 22, the head portion 15a of the guide wire 15 falls down into the wide slit 26b on the plane of the engaging piece 26A, and the guide wire 15 enters into the narrow slit 26a (FIG. 16b). The head portion 15a of the guide wire 15 is further inserted (FIG. 16c). Finally the head portion 15a of the guide wire 15 reaches the distal end of the PEG tube 21 and appears outside, the distal end of the PEG tube 21 being disposed outside the oral cavity of the patient. The head portion 15a of the guide wire 15 is engaged with the socket 13 of the infection preventive cover 10 using the pin 14 as described above (see FIGS. 7a and 7b).

When the engagement of the head portion 15a of the guide wire 15 by the pin 14 is released, and the guide wire 15 is pulled from the outside of the abdomen of the patient, the guide wire 15 (head portion 15a) returns to the position of the tapered portion 22 (FIG. 17a). The head portion 15a of the guide wire 15 is engaged with the narrow slit 26a of the engaging piece 26A at the top end of the connecting member 26. Even if the guide wire 15 is pulled, the guide wire 15 is prevented from being drawn out the engaging piece 26A (FIG. 17b, FIG. 19).

In the above embodiment, the engaging piece 26A is formed integrally with the connecting member 26. However the engaging piece 26A may be formed separately form the connecting member 26 and may be embedded into (or sandwiched by) the top end portion of the connecting member 26. The engaging piece 26A is made of the same material as that of the connecting member 26 (for example, resin, plastic or the like) in a case where the engaging piece 26A is formed integrally with the connecting member 26. Not only resin or plastic but also metal (iron, aluminum or the like) may be used to manufacture the engaging piece 26A in a case where the engaging piece 26A is formed separately from the connecting member 26.

Figure 20:
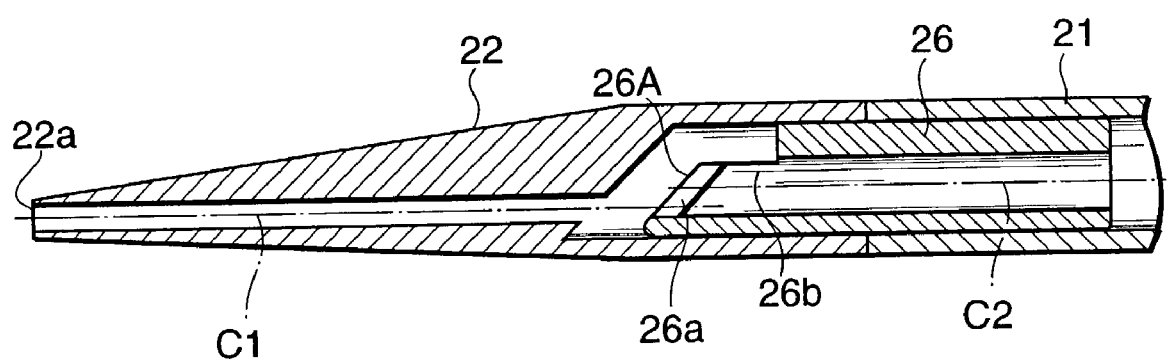
FIG. 20 is a cross-sectional view showing another example of a tapered portion provided on a top end of a PEG catheter.

FIG. 20 illustrates relation between a center line of the tapered portion 22 and a center line of the connecting member 26. The center line C1 of a through hole which the guide wire 15 passes through and which is continued from the opening 22a formed at the top end of the tapered portion 22 is deviated (shifted) downward (lower side) (in a direction to the lower side of the engaging piece 26A) from the center line C2 of the hollow space of the connecting piece 26 (the center line of the PEG tube 21). In FIG. 20, in order to easily understand, the center line C1 of the hole of the tempered portion 22 and the center line C2 of the hallow space in the connecting member 26 are depicted by dots-and-dash lines.

When the guide wire 15 is pulled, the head portion 15a of the guide wire 15 is surely engaged with the lower part of the engaging piece 26A. Even if the guide wire 15 is swung up and down, or the guide wire 15 is slacked, the movement of the main portion of the guide wire 15 (namely, whole portion of the guide wire 15 except for the top head portion 15a) is limited by the throughhole including the opening 22a, so that the top head portion 15a of the guide wire 15 is prevented from being drawn out of the wide slit 26b of the engaging piece 26A. In this way the guide wire 15 and the PEG catheter 20 are securely connected to each other. The relation in which two center lines are deviated from each other is true for the structure shown in FIGS. 16 to 19 (the center line of the PEG tube 21 is substantially coincide with the center line of the tapered portion 22). A shown in FIGS. 18d and 18e, the hole is formed at a position deviated (eccentric) from the center of the connecting member 26.

In another usage method of the infection preventive cover, a guide wire 15 is inserted into a stomach through an outer tube 33 pierced through a wall of an abdomen and a wall of the stomach of a patient. The guide wire 15 is pulled through an esophagus and an oral cavity into a space outside the patient. In this state, a distal end of the guide wire is maintained outside the outer tube 33. A top end 15a of the guide wire 15 pulled outside the oral cavity of the patent is joined with a top end (a conical top portion 22) of a percutaneous endoscopic gastrostomy (PEG) catheter 20 (PEG tube 21) as shown in FIG. 17b. The PEG catheter 20 is delivered from the mouth (oral cavity) into the stomach of the patient by pulling or pushing the guide wire 15 in a state where the catheter 20 is enclosed with an infection preventive cover 10 (tubular flexible sheath 11). Of course, prior to the delivery of the PEG catheter 20 into the stomach from the mouth of the patient, the PEG catheter 20 is entirely enclosed with the infection preventive cover 10 including the long-and-slender tubular sheath 11 and an in-stomach remaining member 23 provided at a distal end of the PEG catheter 20 is fixed to a distal end portion of the infection preventive cover 10 (tubular sheath 11) using a first engaging mechanism including a pin 14.

After the PEG catheter 20 is delivered through the oral cavity into the stomach with the PEG catheter 20 covered with the infection preventive cover 10, the in-stomach remaining member 23 is released from the distal end portion of the infection preventive cover 10 in a space outside the oral cavity, and further the guide wire 15 is drawn into a space outside the body of the patient (for example, by pulling the distal end of the guide wire 15). The PEG catheter 20 is drawn through the top end of the tubular sheath 11 in the stomach. The PEG catheter 20 is drawn through the stomach wall and the abdomen wall (wound) into a space outside the patient together with the outer tube 33. Thereafter the infection preventive cover 10 is removed from the oral cavity into a space outside the patient. The in-stomach remaining member 23 at the distal end of the PEG catheter 20 is left in the stomach (inclusive of a case where the in-stomach remaining member 23 is cut off from the tube 21 of the PEG catheter).

What is claimed is:

1. An infection preventive cover comprising:
    a long-and-slender flexible tubular sheath;
    a first engaging mechanism, the first engaging mechanism engaging an in-stomach remaining member of a distal end of a percutaneous endoscopic gastrostomy catheter adapted for use with the infection preventive cover, the percutaneous endoscopic gastrostomy catheter being disposed within the tubular sheath; and
    a second engaging mechanism, which fixes a top end of a guidewire to the distal end portion of the tubular sheath,
    wherein the first engaging mechanism includes a first pin penetrating a circumferential wall of the distal end portion of the tubular sheath in a radial direction thereof, and the in-stomach remaining member is fixed to the distal end portion of the tubular sheath by being engaged with the first pin.

2. The infection prevention cover according to claim 1, wherein the tubular sheath is provided with a closing film covering an opening at the top end thereof.

3. An infection preventive cover comprising:
    a long-and-slender flexible tubular sheath;
    a first engaging mechanism, the first engaging mechanism engaging an in-stomach remaining member of a distal end of a percutaneous endoscopic gastrostomy catheter adapted for use with the infection preventive cover, the percutaneous endoscopic gastrostomy catheter being disposed within the tubular sheath; and a second engaging mechanism, which fixes a top end of a guidewire to the distal end portion of the tubular sheath, wherein the first engaging mechanism includes a first pin, the tubular sheath includes a hole, into which the first pin is inserted in a radial direction on a circumferential wall of the distal end portion thereof, and the in-stomach remaining member is fixed to the distal end portion of the tubular sheath by being engaged with the first pin inserted into the first hole.

4. An infection preventive cover comprising:

a long-and-slender flexible tubular sheath;

a first engaging mechanism, the first engaging mechanism engaging an in-stomach remaining member of a distal end of a percutaneous endoscopic gastrostomy catheter adapted for use with the infection preventive cover, the percutaneous endoscopic gastrostomy catheter being disposed within the tubular sheath; and a second engaging mechanism, which fixes a top end of a guidewire to the distal end portion of the tubular sheath, wherein said guide wire is inserted into the top end of the catheter disposed inside of the tubular sheath, passes therethrough and appears outside of the catheter at the distal end thereof.

5. The infection preventive cover according to claim 4, wherein the second engaging mechanism includes a second engaging member provided on the distal end portion of the tubular sheath, the top end of the guide wire is fixed to the distal end portion of the tubular sheath with a head portion, a hook portion or a ring or loop portion of the top end of the guide wire being engaged with the second engaging member.

6. The infection prevention cover according to claim 5, wherein the tubular sheath is provided with a closing film covering an opening at the top end thereof.

7. The infection preventive cover according to claim 4, wherein the second engaging mechanism includes a second pin penetrating the circumferential wall of the distal end portion of the tubular sheath in a radial direction thereof, the second pin includes a wide slit section allowing a large diameter head formed at the top end of the guide wire to pass therethrough and a narrow slit section formed continuous with the wide slit section and preventing the head from passing therethrough, and the top end of the guide wire is fixed to the distal end portion of the tubular sheath with the head of the guide wire which has passed through the wide slit section being engaged with the second pin at the narrow slit section.

8. The infection prevention cover according to claim 7, wherein the tubular sheath is provided with a closing film covering an opening at the top end thereof.

9. The infection preventive cover according to claim 4, wherein the second engaging mechanism includes a second pin, the tubular sheath includes a second pin hole for inserting the second pin in a radial direction on the circumferential wall of the distal end portion of the tubular sheath, the second pin includes a wide slit section allowing a large diameter head formed at the top end of the guide wire to pass therethrough and a narrow slit section formed continuous with the wide slit section and preventing the head from passing therethrough, and the top end of the guide wire is fixed to the distal end portion of the tubular sheath with the head of the guide wire which has passed through the wide slit section being engaged with the second pin, which is inserted into the second pin hole, at the narrow slit section.

10. The infection prevention cover according to claim 9, wherein the tubular sheath is provided with a closing film covering an opening at the top end thereof.

11. The infection prevention cover according to claim 4, wherein the tubular sheath is provided with a closing film covering an opening at the top end thereof.

12. An infection preventive cover comprising:

a long-and-slender flexible tubular sheath;

a first engaging mechanism, the first engaging mechanism engaging an in-stomach remaining member of a distal end of a percutaneous endoscopic gastrostomy catheter adapted for use with the infection preventive cover, the percutaneous endoscopic gastrostomy catheter being disposed within the tubular sheath; and a second engaging mechanism, which fixes a top end of a guidewire to the distal end portion of the tubular sheath, wherein the tubular sheath is provided with a closing film covering an opening at the top end thereof.

13. The infection preventive cover according to claim 12, wherein the closing film includes a slit or a pin hole.

14. An infection preventive cover including:

a long-and-slender flexible tubular sheath;

a first engaging mechanism; and a second engaging mechanism, wherein the first engaging mechanism engages an in-stomach remaining member provided on an end of a percutaneous endoscopic gastrostomy catheter adapted for use with the infection preventive cover and disposed within the tubular sheath with a distal end portion of the tubular sheath, and wherein the second engaging mechanism engages a head portion, hook portion, or ring or loop portion formed on a top end of a guide wire which is inserted into the top of the catheter disposed within the tubular sheath, passes therethrough and appears outside of the catheter at the distal end thereof with the distal end portion of the tubular sheath.

15. The infection preventive cover according claim 14, wherein the first engaging mechanism and the second engaging mechanism share in a common engaging mechanism, wherein the common engaging mechanism includes a pin which is formed with a wide slit section allowing a large diameter head formed at the top end of the guide wire to pass therethrough and a narrow slit section formed continuous with the wide slit section and preventing the head from passing therethrough, wherein the tubular sheath is formed with a pin hole for inserting the pin in a radial direction at a circumferential wall of the distal end portion of the tubular sheath, wherein the in-stomach remaining member is fixed to the distal end portion of the tubular sheath by engaging with the pin which is inserted into the pin hole, and wherein the top end of the guide wire is fixed to the distal end portion of the tubular sheath with the head of the guide wire which has passed through the wide slit section being engaged with the pin at the narrow slit section.

16. An infection preventive cover comprising:

a long-and-slender flexible tubular sheath;

a first engaging mechanism, the first engaging mechanism engaging an in-stomach remaining member of a distal end of a percutaneous endoscopic gastrostomy catheter adapted for use with the infection preventive cover, the percutaneous endoscopic gastrostomy catheter being disposed within the tubular sheath;

a second engaging mechanism, which fixes a top end of a guidewire to the distal end portion of the tubular sheath; and a socket formed at a distal end of said flexible tubular sheath.

17. The infection preventive cover according to claim 16, wherein said socket comprises a substantially truncated conical portion and a substantially cylindrical portion formed to an end of the substantially truncated conical portion.

18. The infection preventive cover according to claim 17, wherein the substantially truncated conical portion has a first opening and the socket includes a second opening adjacent the distal end of said flexible tubular sheath, wherein the first opening is larger than the second opening.

19. The infection preventive cover according to claim 16, wherein the socket is integral with the distal end of the flexible tubular sheath.

20. The infection preventive cover according to claim 16, further comprising pin receiving holes disposed on the substantially cylindrical portion.

21. An infection preventive cover comprising a long-and-slender flexible tubular sheath having a guide wire engaging mechanism for fixing the top end of a guide wire, which is inserted into the top end of a percutaneous endoscopic gastrostomy catheter disposed inside of said tubular sheath, passes therethrough and appears outside of the catheter at the distal end thereof, to the distal end portion of said tubular sheath, the percutaneous endoscopic gastrostomy catheter being adapted for use with the infection preventive cover,
wherein the guide wire engaging mechanism includes an engaging member provided on the distal end portion of the tubular sheath, the top end of the guide wire is fixed to the distal end portion of the tubular sheath with a head portion, a hook portion or a ring or loop portion of the top end of the guide wire being engaged with the engaging member.

22. An infection preventive cover comprising a long-and-slender flexible tubular sheath having a guide wire engaging mechanism for fixing the top end of a guide wire, which is inserted into the top end of a percutaneous endoscopic gastrostomy catheter disposed inside of said tubular sheath, passes therethrough and appears outside of the catheter at the distal end thereof, to the distal end portion of said tubular sheath, the percutaneous endoscopic gastrostomy catheter being adapted for use with the infection preventive cover,
wherein the guide wire engaging mechanism includes a pin penetrating the circumferential wall of the distal end portion of the tubular sheath in a radial direction thereof, the pin includes a wide slit section allowing a large diameter head formed at the top end of the guide wire to pass therethrough and a narrow slit section formed continuous with the wide slit section and preventing the head from passing therethrough, and the top end of the guide wire is fixed to the distal end portion of the tubular sheath with the head of the guide wire which has passed through the wide slit section being engaged with the pin at the narrow slit section.

* * * * *